(12) United States Patent
Wolf et al.

(10) Patent No.: US 7,604,378 B2
(45) Date of Patent: Oct. 20, 2009

(54) COLOR CHANGING OUTDOOR LIGHTS WITH ACTIVE INGREDIENT AND SOUND EMISSION

(75) Inventors: Jeffrey J. Wolf, Racine, WI (US); Scott D. Walter, Twin Lakes, WI (US); Scott W. Demarest, Caledonia, WI (US); Darren K. Robling, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/548,940

(22) Filed: Oct. 12, 2006

(65) Prior Publication Data

US 2007/0109763 A1 May 17, 2007

Related U.S. Application Data

(63) Continuation-in-part of application No. 11/426,055, filed on Jun. 23, 2006, now Pat. No. 7,318,659, which is a continuation-in-part of application No. 11/069,964, filed on Mar. 3, 2005, now Pat. No. 7,246,919, said application No. 11/426,055 is a continuation-in-part of application No. 10/561,822, filed on Apr. 25, 2006.

(60) Provisional application No. 60/549,154, filed on Mar. 3, 2004, provisional application No. 60/483,913, filed on Jul. 2, 2003.

(51) Int. Cl.
*F21V 33/00* (2006.01)
(52) U.S. Cl. ................. 362/253; 362/85; 362/227
(58) Field of Classification Search ................. 362/253, 362/85, 86, 231
See application file for complete search history.

(56) References Cited

U.S. PATENT DOCUMENTS 1,535,486 A    4/1925  Lundy (Continued)

FOREIGN PATENT DOCUMENTS

WO    WO 01/78488 A2    10/2001

(Continued)

OTHER PUBLICATIONS

PCT/US2007/021798 International Search Report and Written Opinion dated May 8, 2008.

(Continued)

*Primary Examiner*—Sandra L O'Shea
*Assistant Examiner*—Evan Dzierzynski
(74) *Attorney, Agent, or Firm*—Miller, Matthias & Hull

(57) ABSTRACT

An outdoor light system comprising a plurality light elements linked to a central controller. Each light element include a translucent shell, plurality of LEDs positioned so as to emit a light show through the shell. A compartment for receiving and securing a replaceable volatile active cartridge and a heater for enabling the device to effectively emit an active ingredient from the cartridge when the cartridge is secured in the compartment. A white light source may be provided in each device as a source of illumination along with the LEDs The devices can be used as white light sources, for displaying a coordinated colored light shows, for displaying colored light schemes and for volatile active emission. The devices of disclosed the system may include an acoustic transducer for producing light and sound shows. The device may also include a light sensor, a motion detector and/or a microphone or acoustic receiver thereby enabling the light and sound shows to be dependent upon ambient light intensity, motion detection and/or ambient noise. The devices and systems are suitable for outdoor home lighting, porch and deck lighting and path/driveway lighting.

20 Claims, 9 Drawing Sheets

U.S. PATENT DOCUMENTS

| | | | |
|---|---|---|---|
| 1,565,500 A | 12/1925 | Ritter | |
| 1,706,939 A | 3/1929 | Rosenthal | |
| 1,732,707 A | 10/1929 | Winsboro | |
| 1,920,599 A | 8/1933 | Schuh | |
| 2,124,543 A | 7/1938 | Clyne | |
| 2,143,246 A | 1/1939 | McGary | |
| 2,372,371 A | 3/1945 | Eisner | |
| 2,435,756 A | 2/1948 | Schlesinger | |
| 2,468,164 A | 4/1949 | Brewster | |
| 2,469,656 A | 5/1949 | Lienert | |
| 2,535,802 A | 12/1950 | Libson | |
| 2,694,771 A | 11/1954 | Cox | |
| 2,741,812 A | 4/1956 | Tellier | |
| 2,741,813 A | 4/1956 | Rubin | |
| 2,757,278 A | 7/1956 | Cloud | |
| 2,799,166 A | 7/1957 | Leftwich | |
| 2,818,770 A | 1/1958 | Cilurzo | |
| 2,931,880 A | 4/1960 | Yaffe | |
| 3,080,624 A | 3/1963 | Weber, III | |
| 3,119,565 A | 1/1964 | Nottingham | |
| 3,377,126 A | 4/1968 | Nijland et al. | |
| 3,760,179 A | 9/1973 | Addington, Jr. | |
| 3,763,347 A | 10/1973 | Whitaker | |
| 3,923,458 A | 12/1975 | Moran | |
| 3,948,445 A | 4/1976 | Andeweg | |
| 4,009,384 A | 2/1977 | Holland | |
| 4,045,664 A | 8/1977 | Vrenken et al. | |
| 4,184,099 A | 1/1980 | Lindauer et al. | |
| 4,234,907 A | 11/1980 | Daniel | |
| 4,346,059 A | 8/1982 | Spector | |
| 4,391,781 A | 7/1983 | van Lit | |
| 4,463,286 A | 7/1984 | Justice | |
| 4,493,011 A | 1/1985 | Spector | |
| 4,510,555 A | 4/1985 | Mori | |
| 4,519,017 A | 5/1985 | Daniel | |
| 4,544,592 A | 10/1985 | Spector | |
| 4,549,250 A | 10/1985 | Spector | |
| 4,561,043 A | 12/1985 | Thompson | |
| 4,579,717 A | 4/1986 | Gyulay | |
| 4,640,266 A | 2/1987 | Levy | |
| 4,647,428 A | 3/1987 | Gyulay | |
| 4,647,433 A | 3/1987 | Spector | |
| 4,714,984 A | 12/1987 | Spector | |
| 4,754,372 A | 6/1988 | Harrison | |
| 4,849,181 A | 7/1989 | Kelley et al. | |
| 4,849,606 A | 7/1989 | Martens, III et al. | |
| 4,875,144 A | 10/1989 | Wainwright | |
| 4,885,663 A | 12/1989 | Parker | |
| 4,933,815 A | 6/1990 | Parthasarathy | |
| 4,955,975 A | 9/1990 | Mori | |
| 4,962,687 A * | 10/1990 | Belliveau et al. | 84/464 R |
| 4,965,490 A | 10/1990 | Ratner | |
| 4,965,701 A | 10/1990 | Voland | |
| 4,972,305 A | 11/1990 | Blackburn | |
| 4,974,136 A | 11/1990 | Noori-Shad et al. | |
| 5,021,928 A | 6/1991 | Daniel | |
| 5,046,837 A | 9/1991 | Stroomer et al. | |
| 5,066,085 A | 11/1991 | Gimbutas et al. | |
| 5,069,877 A | 12/1991 | Pozzo | |
| 5,178,839 A | 1/1993 | Spector | |
| 5,183,323 A | 2/1993 | Daniel | |
| 5,217,696 A | 6/1993 | Wolverton et al. | |
| 5,247,491 A | 9/1993 | Kwiatkowski | |
| 5,249,105 A | 9/1993 | Koizumi | |
| 5,251,116 A | 10/1993 | Wijbenga et al. | |
| 5,301,090 A | 4/1994 | Hed | |
| 5,402,517 A | 3/1995 | Gillett et al. | |
| 5,426,474 A | 6/1995 | Rubtsov et al. | |
| 5,432,876 A | 7/1995 | Appeldorn et al. | |
| D363,537 S | 10/1995 | Moody | |
| 5,455,750 A | 10/1995 | Davis et al. | |
| 5,547,616 A | 8/1996 | Dancs et al. | |
| 5,556,191 A | 9/1996 | Maassen | |
| 5,561,346 A | 10/1996 | Byrne | |
| 5,568,964 A | 10/1996 | Parker et al. | |
| 5,647,052 A | 7/1997 | Patel et al. | |
| 5,651,942 A | 7/1997 | Christensen | |
| 5,683,762 A * | 11/1997 | Banschick | 428/4 |
| 5,688,042 A | 11/1997 | Madadi et al. | |
| 5,691,886 A | 11/1997 | Stacy | |
| 5,703,440 A | 12/1997 | Kachmarik et al. | |
| 5,711,591 A | 1/1998 | Jordan | |
| 5,801,484 A | 9/1998 | Bankuti et al. | |
| 5,823,652 A | 10/1998 | Vann | |
| 5,908,231 A | 6/1999 | Huff | |
| 6,016,038 A | 1/2000 | Mueller et al. | |
| 6,099,137 A | 8/2000 | McCormack et al. | |
| 6,106,786 A | 8/2000 | Akahoshi | |
| 6,120,737 A | 9/2000 | Zembrodt | |
| 6,143,313 A | 11/2000 | Ito et al. | |
| 6,150,774 A | 11/2000 | Mueller et al. | |
| 6,166,496 A | 12/2000 | Lys et al. | |
| 6,186,637 B1 * | 2/2001 | Murrietta | 362/101 |
| 6,200,002 B1 | 3/2001 | Marshall et al. | |
| 6,211,626 B1 | 4/2001 | Lys et al. | |
| 6,217,188 B1 | 4/2001 | Wainwright et al. | |
| 6,220,722 B1 | 4/2001 | Begemann | |
| 6,220,742 B1 | 4/2001 | Lloyd et al. | |
| 6,234,645 B1 | 5/2001 | Borner et al. | |
| 6,234,648 B1 | 5/2001 | Borner et al. | |
| 6,234,649 B1 | 5/2001 | Katougi | |
| 6,254,248 B1 | 7/2001 | McAuley et al. | |
| 6,270,720 B1 | 8/2001 | Mandish | |
| 6,292,901 B1 | 9/2001 | Lys et al. | |
| 6,294,800 B1 | 9/2001 | Duggal et al. | |
| 6,299,338 B1 | 10/2001 | Levinson et al. | |
| 6,318,876 B1 | 11/2001 | Sigro et al. | |
| 6,339,298 B1 | 1/2002 | Chen | |
| 6,340,868 B1 | 1/2002 | Lys et al. | |
| 6,371,450 B1 | 4/2002 | Davis et al. | |
| 6,371,634 B1 | 4/2002 | Tufte | |
| D457,667 S | 5/2002 | Piepgras et al. | |
| D457,669 S | 5/2002 | Piepgras et al. | |
| D457,974 S | 5/2002 | Piepgras et al. | |
| 6,391,329 B1 | 5/2002 | Ito et al. | |
| D458,395 S | 6/2002 | Piepgras et al. | |
| 6,400,104 B1 | 6/2002 | Ham | |
| 6,402,347 B1 | 6/2002 | Maas et al. | |
| 6,406,172 B1 | 6/2002 | Harbers et al. | |
| 6,416,180 B1 | 7/2002 | Strobl | |
| 6,417,439 B2 * | 7/2002 | Uehara et al. | 84/645 |
| D463,610 S | 9/2002 | Piepgras et al. | |
| 6,459,919 B1 | 10/2002 | Lys et al. | |
| 6,472,876 B1 | 10/2002 | Notohamiprodjo et al. | |
| 6,478,440 B1 | 11/2002 | Jaworski et al. | |
| 6,478,453 B2 | 11/2002 | Lammers et al. | |
| 6,480,649 B2 | 11/2002 | Lee | |
| D468,035 S | 12/2002 | Blanc et al. | |
| 6,488,393 B1 | 12/2002 | Burnham | |
| 6,499,860 B2 | 12/2002 | Begemann | |
| 6,513,954 B2 | 2/2003 | Ebersole | |
| 6,528,954 B1 | 3/2003 | Lys et al. | |
| 6,536,910 B2 | 3/2003 | Lin | |
| 6,536,914 B2 | 3/2003 | Hoelen et al. | |
| 6,539,656 B2 | 4/2003 | Maas et al. | |
| 6,543,925 B2 | 4/2003 | Kuykendal et al. | |
| 6,547,416 B2 | 4/2003 | Pashley et al. | |
| 6,547,423 B2 | 4/2003 | Marshall et al. | |
| 6,548,967 B1 | 4/2003 | Dowling et al. | |
| 6,558,022 B2 | 5/2003 | Kawahara | |
| 6,573,536 B1 | 6/2003 | Dry | |
| 6,577,080 B2 | 6/2003 | Lys et al. | |
| 6,586,882 B1 | 7/2003 | Harbers | |
| 6,601,982 B1 | 8/2003 | Begemann et al. | |

| | | | | | | |
|---|---|---|---|---|---|---|
| 6,608,453 | B2 | 8/2003 | Morgan et al. | 7,093,958 B2 | 8/2006 | Coushaine |
| 6,613,288 | B2 | 9/2003 | Gupte | 7,104,679 B2 | 9/2006 | Shin et al. |
| 6,624,597 | B2 | 9/2003 | Dowling et al. | 7,109,665 B2 | 9/2006 | Green |
| 6,626,554 | B2 | 9/2003 | Rincover et al. | 7,116,294 B2 | 10/2006 | Stopa |
| 6,627,857 | B1 | 9/2003 | Tanner et al. | 7,160,012 B2 | 1/2007 | Hilscher et al. |
| 6,628,885 | B1 | 9/2003 | Wilkie et al. | 7,175,302 B2 | 2/2007 | Kazar et al. |
| 6,629,772 | B2 | 10/2003 | Brunfeld | 2001/0014019 A1 | 8/2001 | Begemann |
| 6,642,669 | B1 | 11/2003 | MacAdam et al. | 2001/0035853 A1 | 11/2001 | Hoelen et al. |
| 6,648,486 | B2 | 11/2003 | Harbers et al. | 2001/0038532 A1 | 11/2001 | Harbers et al. |
| 6,648,496 | B1 | 11/2003 | Elghoroury et al. | 2001/0049893 A1 | 12/2001 | Maas et al. |
| 6,655,824 | B2 | 12/2003 | Tufte | 2002/0006044 A1 | 1/2002 | Harbers et al. |
| 6,672,734 | B2 | 1/2004 | Lammers | 2002/0030997 A1 | 3/2002 | Tufte |
| 6,676,282 | B2 | 1/2004 | Begemann et al. | 2002/0048169 A1* | 4/2002 | Dowling et al. ............. 362/234 |
| 6,688,753 | B2 | 2/2004 | Calon et al. | 2002/0071285 A1 | 6/2002 | Tufte |
| 6,712,494 | B1 | 3/2004 | Hodge | 2002/0075671 A1 | 6/2002 | Tufte |
| 6,717,376 | B2 | 4/2004 | Lys et al. | 2002/0075674 A1 | 6/2002 | Tufte |
| 6,720,745 | B2 | 4/2004 | Lys et al. | 2002/0105800 A1 | 8/2002 | Tufte |
| 6,726,341 | B2 | 4/2004 | Pashley et al. | 2002/0118538 A1* | 8/2002 | Calon et al. ................. 362/236 |
| 6,733,161 | B2 | 5/2004 | Tufte | 2002/0131273 A1 | 9/2002 | Tufte |
| D491,678 | S | 6/2004 | Piepgras et al. | 2002/0135997 A1 | 9/2002 | Lammers |
| D492,042 | S | 6/2004 | Piepgras et al. | 2002/0136017 A1 | 9/2002 | Tufte |
| 6,742,914 | B2 | 6/2004 | Prodell | 2002/0141058 A1 | 10/2002 | Itoh |
| 6,745,506 | B2 | 6/2004 | Maas et al. | 2003/0007887 A1 | 1/2003 | Roumpos et al. |
| 6,758,573 | B1 | 7/2004 | Thomas et al. | 2003/0021117 A1 | 1/2003 | Chan |
| 6,774,584 | B2 | 8/2004 | Lys et al. | 2003/0039115 A1 | 2/2003 | Lin |
| 6,777,891 | B2 | 8/2004 | Lys et al. | 2003/0046842 A1 | 3/2003 | Maas et al. |
| 6,779,905 | B1* | 8/2004 | Mazursky et al. ............ 362/101 | 2003/0071932 A1 | 4/2003 | Tanigaki |
| 6,781,329 | B2 | 8/2004 | Mueller et al. | 2003/0078791 A1 | 4/2003 | Tufte |
| 6,788,011 | B2 | 9/2004 | Mueller et al. | 2003/0095409 A1 | 5/2003 | Cheng |
| 6,793,360 | B2 | 9/2004 | Goslee | 2003/0107887 A1* | 6/2003 | Eberl ......................... 362/227 |
| 6,796,685 | B1 | 9/2004 | Nemirow | 2003/0209183 A1 | 11/2003 | Tufte |
| 6,801,003 | B2 | 10/2004 | Schanberger et al. | 2003/0231488 A1 | 12/2003 | Albee |
| 6,802,635 | B2 | 10/2004 | Robertson et al. | 2004/0066652 A1 | 4/2004 | Hong |
| 6,806,659 | B1 | 10/2004 | Mueller et al. | 2004/0070967 A1 | 4/2004 | Kennedy |
| 6,815,724 | B2 | 11/2004 | Dry | 2004/0095078 A1 | 5/2004 | Leong |
| 6,817,731 | B2 | 11/2004 | Tufte | 2004/0095754 A1 | 5/2004 | Hsu |
| 6,831,303 | B2 | 12/2004 | Dry | 2004/0095780 A1 | 5/2004 | Reed |
| 6,833,539 | B1 | 12/2004 | Maeda | 2004/0109317 A1 | 6/2004 | Ribarich |
| 6,837,591 | B2 | 1/2005 | Tufte | 2004/0124790 A1 | 7/2004 | Han et al. |
| 6,840,646 | B2 | 1/2005 | Cornelissen et al. | 2004/0179358 A1 | 9/2004 | Tufte |
| 6,848,822 | B2 | 2/2005 | Ballen et al. | 2004/0189218 A1 | 9/2004 | Leong et al. |
| 6,851,844 | B2 | 2/2005 | Guy | 2004/0232825 A1 | 11/2004 | Sorg |
| 6,854,208 | B1 | 2/2005 | Chuang et al. | 2004/0246711 A1 | 12/2004 | Brenchley et al. |
| 6,854,854 | B2 | 2/2005 | Hoelen et al. | 2004/0257798 A1 | 12/2004 | Hart et al. |
| 6,854,869 | B1 | 2/2005 | Fernandez | 2004/0264185 A1 | 12/2004 | Grotsch et al. |
| D503,467 | S | 3/2005 | Flashinski et al. | 2005/0024892 A1 | 2/2005 | Cabrera |
| 6,869,202 | B2 | 3/2005 | Tufte | 2005/0030747 A1 | 2/2005 | Bogdal |
| 6,869,204 | B2 | 3/2005 | Morgan et al. | 2005/0036300 A1 | 2/2005 | Dowling et al. |
| 6,874,909 | B2 | 4/2005 | Vanderschuit | 2005/0047127 A1 | 3/2005 | Tutman |
| 6,880,948 | B2 | 4/2005 | Koch et al. | 2005/0074358 A1 | 4/2005 | Hart et al. |
| 6,883,929 | B2 | 4/2005 | Dowling | 2005/0099108 A1 | 5/2005 | Hofmann et al. |
| 6,883,931 | B2 | 4/2005 | Tufte | 2005/0104503 A1 | 5/2005 | Ellens et al. |
| 6,888,322 | B2 | 5/2005 | Dowling et al. | 2005/0128751 A1 | 6/2005 | Roberge et al. |
| 6,890,085 | B2 | 5/2005 | Hacker | 2005/0135101 A1* | 6/2005 | Richmond ................. 362/276 |
| 6,897,624 | B2 | 5/2005 | Lys et al. | 2005/0162101 A1 | 7/2005 | Leong et al. |
| 6,902,301 | B2 | 6/2005 | Kieronski | 2005/0169015 A1 | 8/2005 | Luk et al. |
| 6,921,184 | B2 | 7/2005 | Tufte | 2005/0169643 A1 | 8/2005 | Franklin |
| 6,936,978 | B2 | 8/2005 | Morgan et al. | 2005/0169666 A1 | 8/2005 | Porchia et al. |
| 6,951,401 | B2 | 10/2005 | Van Hees et al. | 2005/0169812 A1 | 8/2005 | Helf et al. |
| 6,952,079 | B2 | 10/2005 | Shiang et al. | 2005/0173675 A1 | 8/2005 | Schmidt et al. |
| 6,957,897 | B1 | 10/2005 | Nelson et al. | 2005/0174473 A1 | 8/2005 | Morgan et al. |
| 6,965,205 | B2 | 11/2005 | Piepgras et al. | 2005/0185392 A1 | 8/2005 | Walter et al. |
| 6,966,665 | B2 | 11/2005 | Limburg et al. | 2005/0185398 A1 | 8/2005 | Scannell, Jr. |
| 6,976,774 | B2 | 12/2005 | Reiss | 2005/0195598 A1 | 9/2005 | Dancs et al. |
| 7,008,096 | B1 | 3/2006 | Coushaine et al. | 2005/0195600 A1 | 9/2005 | Porchia et al. |
| 7,038,399 | B2 | 5/2006 | Lys et al. | 2005/0207152 A1 | 9/2005 | Maxik |
| 7,046,920 | B2 | 5/2006 | Flashinski | 2005/0213342 A1 | 9/2005 | Tufte |
| 7,052,152 | B2 | 5/2006 | Harbers et al. | 2005/0258439 A1 | 11/2005 | Dry |
| 7,067,981 | B2 | 6/2006 | Nishio et al. | 2005/0258440 A1 | 11/2005 | Dry |
| 7,075,224 | B2 | 7/2006 | Coushaine | 2005/0259416 A1 | 11/2005 | Gauna et al. |
| 7,080,932 | B2 | 7/2006 | Keuper | 2005/0265018 A1 | 12/2005 | Yasuda et al. |
| 7,086,756 | B2 | 8/2006 | Maxik | 2005/0265023 A1 | 12/2005 | Scholl |
| 7,086,767 | B2 | 8/2006 | Sidwell et al. | 2005/0269581 A1 | 12/2005 | Dry |

| | | |
|---|---|---|
| 2005/0275626 A1 | 12/2005 | Mueller et al. |
| 2005/0281030 A1 | 12/2005 | Leong et al. |
| 2005/0285538 A1 | 12/2005 | Jaworski et al. |
| 2006/0001677 A1 | 1/2006 | Webb et al. |
| 2006/0002102 A1 | 1/2006 | Leonard |
| 2006/0002110 A1 | 1/2006 | Dowling et al. |
| 2006/0006784 A1 | 1/2006 | Takahara et al. |
| 2006/0022214 A1 | 2/2006 | Morgan et al. |
| 2006/0023447 A1 | 2/2006 | Justel et al. |
| 2006/0045818 A1 | 3/2006 | Moreland |
| 2006/0055315 A1 | 3/2006 | Bokor et al. |
| 2006/0071589 A1 | 4/2006 | Radkov |
| 2006/0081871 A1 | 4/2006 | Streubel |
| 2006/0082333 A1 | 4/2006 | Laski |
| 2006/0083013 A1 | 4/2006 | Wanninger et al. |
| 2006/0103291 A1 | 5/2006 | Ellens et al. |
| 2006/0114670 A1 | 6/2006 | Ho |
| 2006/0120080 A1 | 6/2006 | Sipinski et al. |
| 2006/0176690 A1 | 8/2006 | Yuen |
| 2006/0220990 A1 | 10/2006 | Coushaine et al. |
| 2006/0226795 A1 | 10/2006 | Walter et al. |
| 2006/0238136 A1 | 10/2006 | Johnson, III et al. |
| 2006/0244000 A1 | 11/2006 | Jager et al. |
| 2006/0248783 A1 | 11/2006 | Lindquist et al. |
| 2006/0275040 A1 | 12/2006 | Franklin |

FOREIGN PATENT DOCUMENTS

| | | |
|---|---|---|
| WO | WO03/026358 A1 | 3/2003 |
| WO | WO2004/023850 A2 | 3/2004 |
| WO | WO 2004/068945 A1 | 8/2004 |
| WO | WO2004071935 A | 8/2004 |
| WO | WO 2004/073399 A1 | 9/2004 |
| WO | WO2005/086245 A2 | 9/2005 |

OTHER PUBLICATIONS

PCT/US2007/021926 International Search Report and Written Opinion dated Apr. 1, 2008.

PCT/US2007/021929 International Search Report and Written Opinion dated Apr. 8, 2008.

* cited by examiner

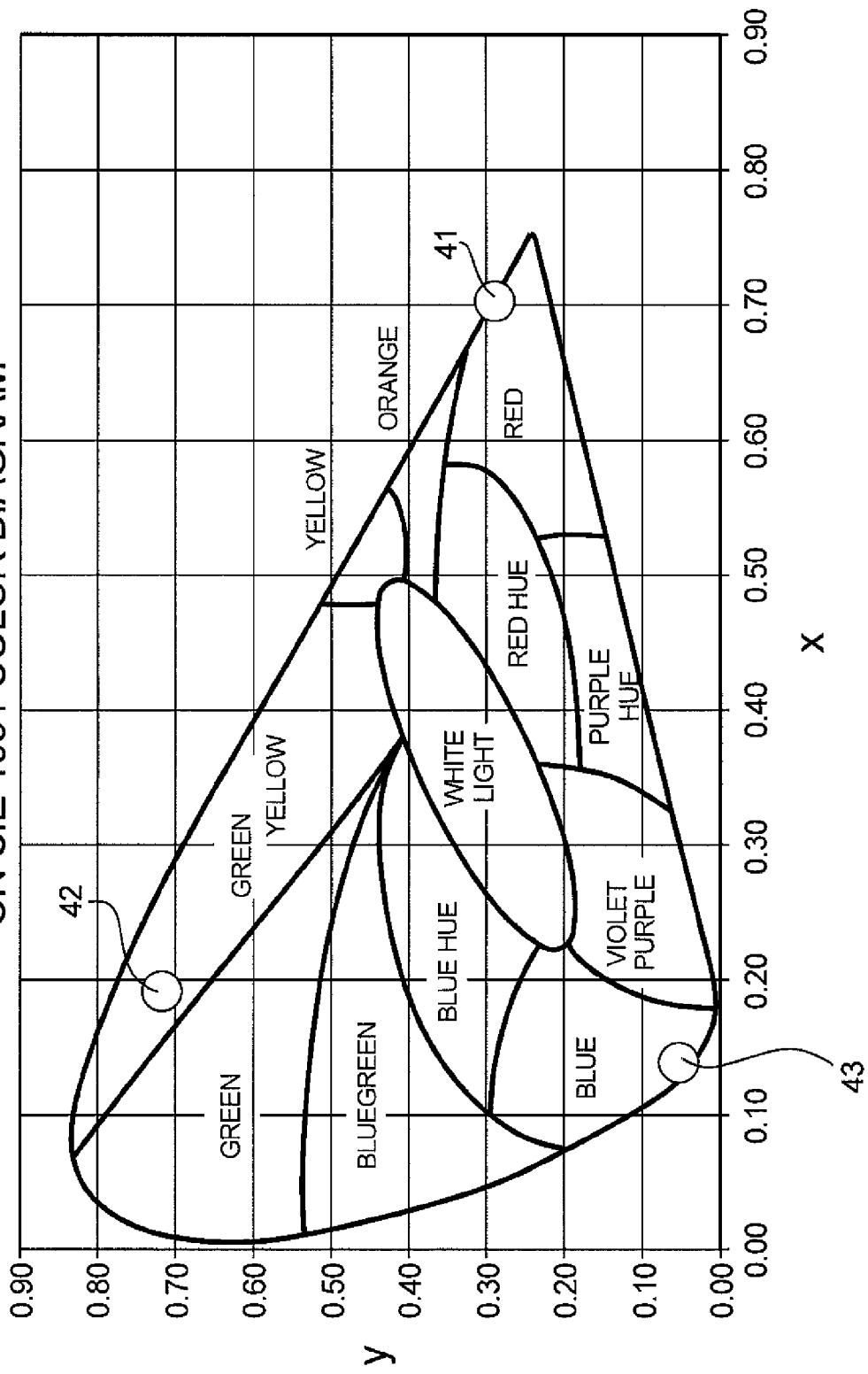

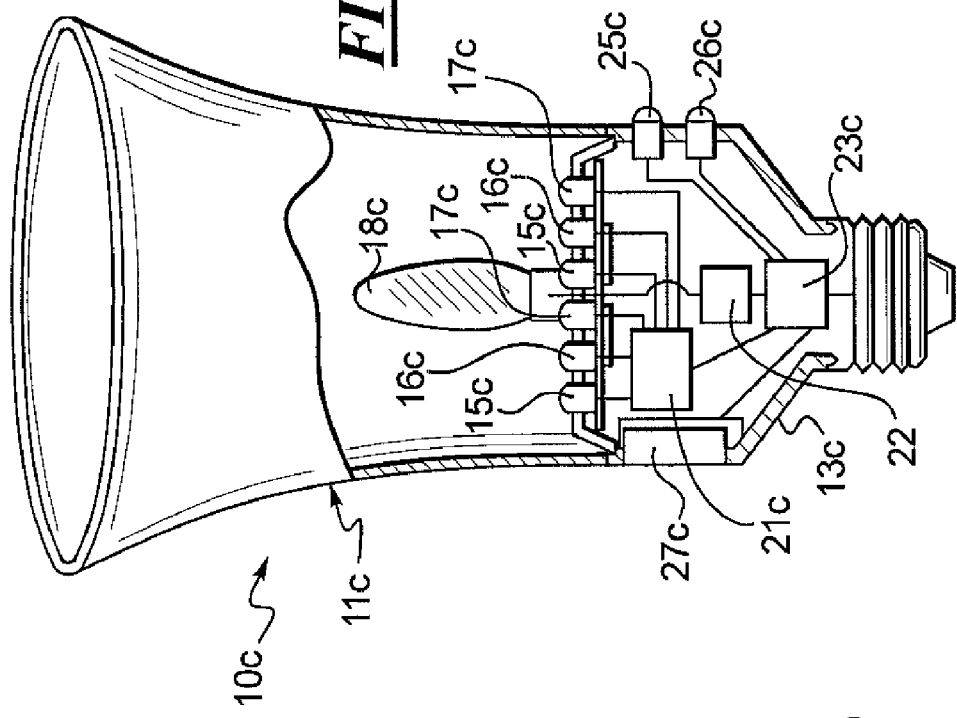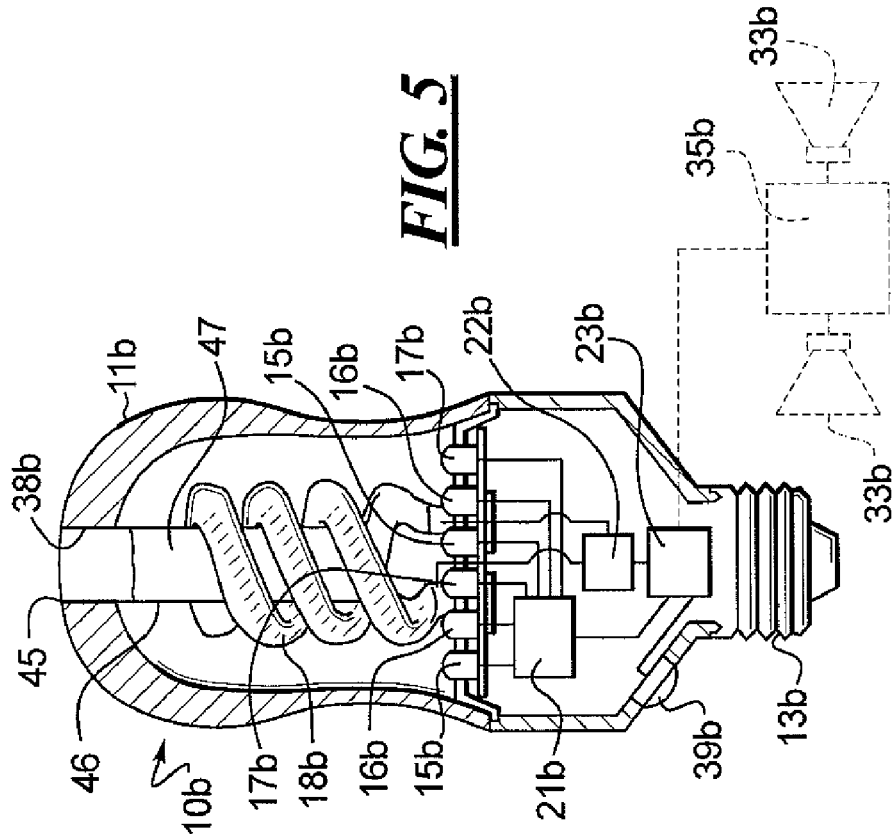

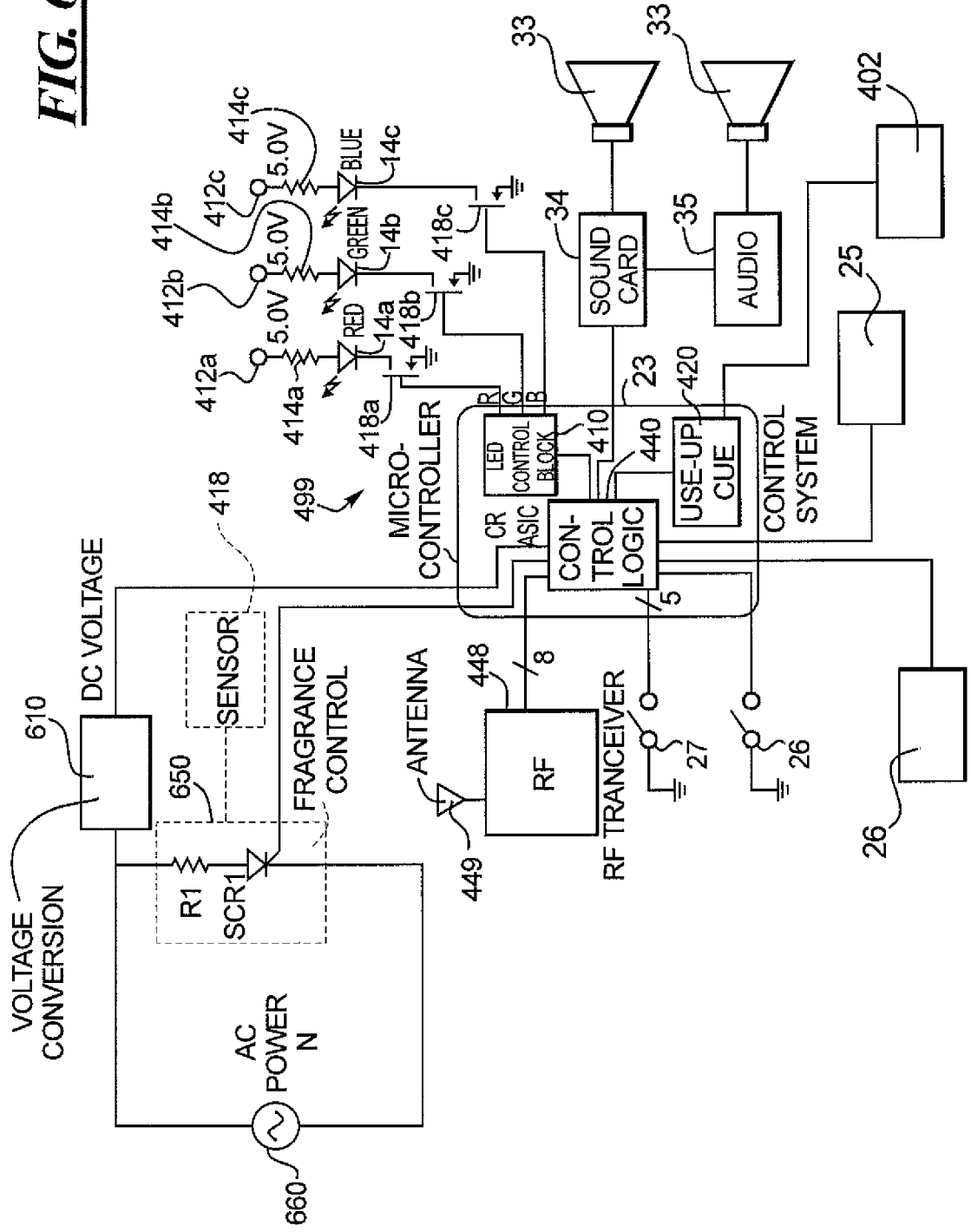

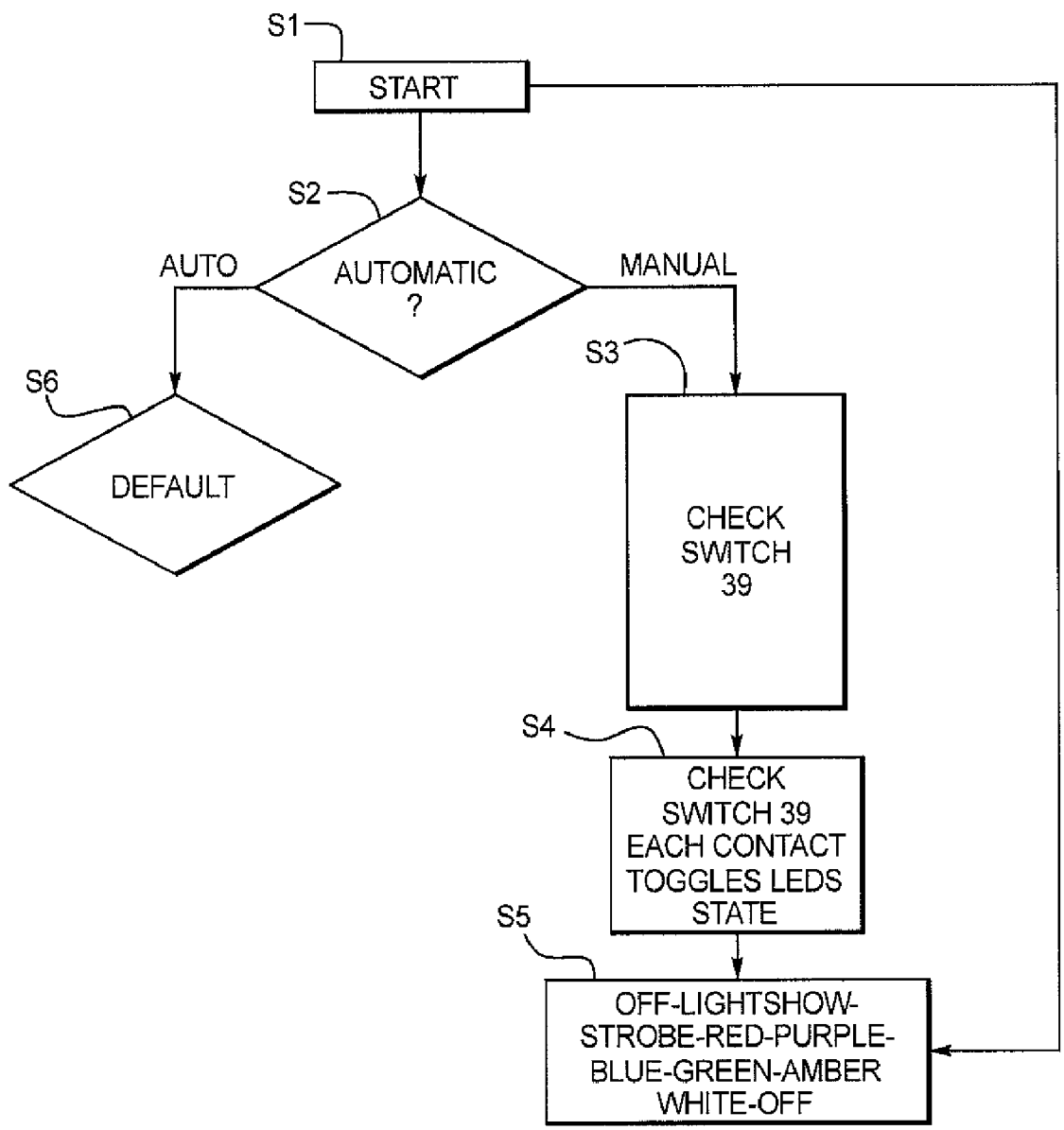

COLOR CHANGING OUTDOOR LIGHTS WITH ACTIVE INGREDIENT AND SOUND EMISSION

CROSS-REFERENCE TO RELATED APPLICATIONS

This application is a continuation-in-part of U.S. patent application Ser. No. 11,426,055, filed on Jun. 23, 2006 now U.S. Pat. No. 7,318,659, which is a continuation-in-part of U.S. patent application Ser. No. 11/069,964, filed on Mar. 3, 2005 now U.S. Pat. No. 7,246,919, which claims priority to Provisional Patent Application Ser. No. 60/549,154, filed on Mar. 3, 2004, and which is also a continuation-in-part of U.S. patent application Ser. No. 10/561,822, filed on Apr. 25, 2006, still pending, which claims priority to Provisional Patent Application Ser. No. 60/483,913 filed on Jul. 2, 2003.

BACKGROUND

1. Technical Field

Alternatives to conventional outdoor lights and light systems are disclosed which provide various combinations of white light, multi-colored light in the form of changing colored light shows through the use of RGB LED clusters, active ingredient vapor emission, sound emission, and which may be responsive to environmental conditions such as ambient sound, motion and light. The disclosed devices can be used in a variety of different applications including as a substitute for a patio, porch and deck light systems, path lighting, architectural light systems and other applications which call for the combination of white light and colored, mood enhancing light with the optional incorporation of sound and active vapor emission, motion, sound and/or temperature detection.

2. Description of the Related Art

Creating a pleasant ambience is a popular aspect of exterior home decor. This is often achieved through one or more combinations of functional lighting, aesthetic architectural lighting, and lighting to enhance or create a certain mood and the use of vaporized actives such as fragrance and/or insect repellant. Conventional products such as citronella candles, tiki torches, low voltage lights, spot lights, outdoor fireplaces and the like are commonly used to create a pleasant backyard, porch or deck environment in the home. While those conventional products help create a pleasant environment and ambiance, they have their drawbacks.

For example, while candles create soft light and fragrance, which creates a pleasant mood, candles present a potential fire hazard and they are often not effective in windy or breezy conditions. Outdoor fireplaces are a fire hazard and generate a substantial amounts of smoke. Restrictions on the use of outdoor candles, tiki torches and outdoor fireplaces may be imposed in fire-prone jurisdictions.

A variety of types of outdoor lights for backyards, porches, and decks ate available but the controls for these products ate relatively primitive and they often attract insects, which is disadvantageous. Traditional outdoor lights, such as floodlights, porch or deck lights, do not provide the colored light effects, fragrance emission and/or other active emission.

Thus, a need exists for the combination of white light and/or colored light with other volatile active emission other than fragrances such as air deodorization, the controlled release of insect repellent, aromatherapy volatiles or other materials, any of which may be combined with fragrant materials if necessary to make an outdoor environment more enjoyable. Further, a need exists for a combination of white light and/or colored light, insect repellent and fragrance for an outdoor patio or deck as well as a combination of outdoor lights that emit insect attractant to keep insects away from a certain area, such the patio or deck.

Further, there is a need for variable colored light and white light in outdoor lighting schemes as well as outdoor lighting systems that are responsive to ambient light and sound. There is also a need for versatile outdoor lighting that can be easily changed for parties and other festivities.

SUMMARY OF THE DISCLOSURE

Therefore, multiple needs exist for light devices an integrated outdoor lighting system that combine two or more of the following functions: white light emission; variable colored light emission; colored light shows; fragrance emission; air sanitization; air deodorization; insect repellent emission; light emission that repels insects; light emission that attracts insects; light/sound/volatile active emission that is responsive to ambient conditions such as light, motion or sound; and any combinations thereof that can be used indoors.

In view of the and drawbacks of the outdoor lighting and fragrance devices and outdoor lighting systems currently on the market, devices are disclosed herein which provide the various combinations of lighting, colored lighting and light shows, the emission of various volatile actives, the generation of sound and responsiveness to the ambient conditions such as light, motion and noise. The disclosed devices can be used outdoors and single units or in coordinated systems and are versatile in design and construction.

One disclosed device is a combination multicolored light/white light/volatile active dispenser/sound transmission device that comprises a base coupled to a white light source and which supports light and sound show circuitry. The base further supports at least one light group comprising red, green and blue lights light sources. The light and sound show circuitry comprise a memory for storing at least one light and sound show. The device further comprises a replaceable cartridge containing an active material and a speaker for transmitting sound. An outer shell is connected to the base and encloses the white light source and red, green and blue lights.

In a refinement, device is part of an integrated outdoor lighting system.

In another refinement the system further comprises a central controller hard-wired or wirelessly coupled to each individual device. The device may be connected in a memory card programmed with at least one light and sound show. The memory card being wirelessly coupled to the light and sound show circuitry by the remote when the memory card is received in the slot.

In another refinement, the light and sound show is dependent upon the volatile active or vice versa.

In a refinement, individual devices or a controller of a system further comprise at least one switch performing one or mote functions selected from the group consisting of: activating the light and sound show and turning off the white light sources; turning on the white light sources and deactivating the light and sound show; turning off both the white light sources and light and sound show; freezing the light and sound show; selecting a light and sound show from a plurality of light and sound shows stored in the memory; adjusting the sound volume; muting the sound; and adjusting active emission.

Individual devices of a system may also include a heater to heat the active cartridge for purposes of volatilizing the active.

In a refinement, the cartridge comprises an indicator that is linked to the light and sound show circuitry. The light and sound show circuitry selects a particular light and sound show or sequence of light and sound shows from the memory based on the indicator of the cartridge.

In a refinement, the active ingredient in the active ingredient cartridge is selected from the group consisting of a fragrance, an air sanitizer, an air deodorizers an insecticide, an insect repellant, an insect attractant, a medicine, an aromatherapy oil, and combinations thereof.

In a refinement, the device further comprises a light or motion sensor that is coupled to the light and sound show circuitry, and the light and sound show circuitry adjusts the light and sound show based upon ambient light, movement, noise or temperature.

In a refinement, the white light source is a fluorescent light and the light control circuitry varies light emitted from the red, green and blue lights to adjust the cumulative light temperature emitted from the device from a cool led light to a warm blue light.

In a refinement, the device further comprises a light or motion sensor that is coupled to the light control circuitry and the light control circuitry adjusts the color scheme based upon ambient light or movement.

A combination white light source, light and sound show generator, air treatment device an in this d acoustic transducer is disclosed which comprises a male base for engaging a light socket. The base supports a white light source, light and sound show circuitry and at least one light group comprising a red, green and blue light cluster. In individual units, the light and sound show circuitry comprises a memory for storing a plurality of light and sound shows. In integrated outdoor light systems, each the main memory and light and sound show storage is part of the controller. Communication between the controller and the individual units or devices can be hardwired or wireless. The individual devices further comprise a replaceable cartridge containing a volatile active. The volatile active is matched with the plurality of light and sound shows. The device further comprise an acoustic transducer for the emission of sound as well as an outer shell that is connected to the base and that encloses the fluorescent lamp and light and sound show circuitry. The individual devices or the central controller further comprise at least one switch performing one or more functions selected from the group consisting of: activating the light and sound show and turning off the white light source; turning on the white light source and deactivating the light and sound show; turning off both the white light source and the light and sound show; freezing the light and sound show; adjusting the volume of the acoustic transducer; muting the acoustic transducer; and scrolling through the plurality of light and sound shows stored in the memory.

In a refinement, an active cartridge is received in a slot disposed in the light bulb-type device and the device further comprises a heater which engages the cartridge when received in the slot. The heater is controlled by the light and sound show circuitry and the current supplied to the heater is dependent upon the active contained within the cartridge.

An outdoor lighting system comprising a plurality of devices described above linked to a central controller and controlled by said central controller.

In a refinement, the outdoor lighting system comprises a plurality of devices as described above with low voltage light elements for low-voltage path lighting.

In another refinement, the devices described above are convertible to floodlights by replacing the outer shell or globe. In a similar refinement, the outer shell or globe may be replaced to provide different light effects.

Other advantages and features will be apparent from the following detailed description when read in conjunction with the attached drawings. As will be apparent from this disclosure, numerous combinations of features can be provided in this disclosure will not attempt to specifically describe every possible combination. Thus, broadly, lighting devices and controlled outdoor light-up systems are disclosed with any plurality of the following features: white light emission; colored light emission; colored light shows; volatile active emission; sound emission; and sound and/or light emission that is responsive to ambient conditions such as motion, light, sound.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 4 shows an exemplary CIE chart with three coordinates corresponding to three LEDs of different colors, red, green and blue, wherein a light show presented in accordance with this disclosure comprises any path disposed within the boundaries of the curve carried out over time.

FIG. 5 is a cross-sectional view of another disclosed outdoor device with a threaded, screw-in base and a coiled fluorescent white light source and that is coupled to an exterior sound system.

FIG. 6 is a circuit diagram of the control mechanisms for the device is shown in FIGS. 1-3 and 5.

FIG. 7 is a flow chart of a program for operating the devices of FIGS. 1-3 and 5.

FIG. 12 is a front sectional view of a floodlight-type device made in accordance with this disclosure.

It should be understood that the drawings are not necessarily to scale and that the disclosed embodiments are sometimes illustrated diagrammatically and in partial views. In certain instances, details which ate not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1:
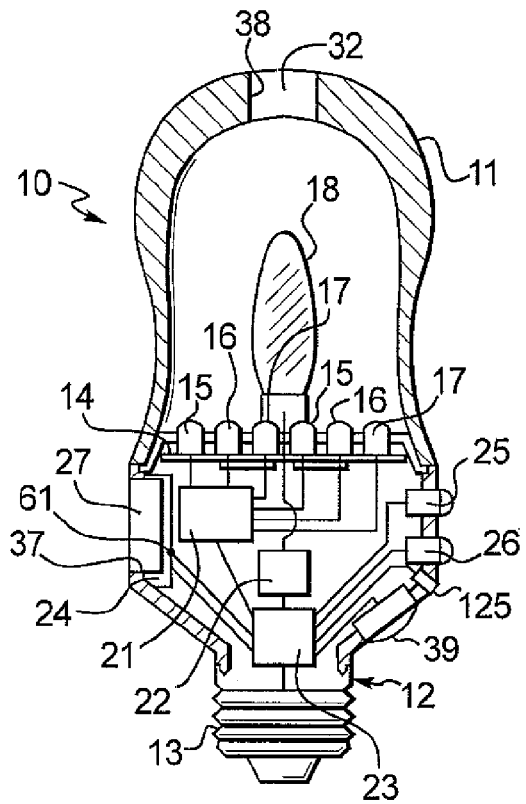
FIG. 1 is a cross-sectional view of a disclosed combination white light/colored light show/active vapor emission/ambient light or motion and sound responsive device with a threaded, screw-in base and an incandescent white light source.

FIG. 1 illustrates a screw-in combination white light/colored light show/active ingredient emission device 10 made in accordance with this disclosure. While the disclosed devices can mate with any one of a number of outdoor lighting fixtures (such as conventional fixtures for receiving incandescent, halogen, or fluorescent bulbs), for exemplary purposes, the description provided herein refers to an Edison-style, screw-in light devices that mate with a conventional incandescent light socket with a threaded female receptacle. Of course, the devices of this disclosure may be embodied in any light bulb that mates with a light socket/power source.

Turning to FIG. 1, the device 10 includes a translucent housing or cover 11 connected to a base 12. The bottom of the base 12 comprises a threaded male, screw-in connector or base 13, which is configured to mate with a threaded female socket of a conventional Edison light socket other lighting fixture. When connector 13 is mated with such a socket, AC power is provided to the device 10 from the lamp or lighting fixture.

The power is provided to an LED base board (light array) 14, on which LEDs 15 (red), 16 (green), and 17 (blue), ate mounted along with a light incandescent bulb 18. The LEDs may be provided in three diode clusters of red, green and blue diodes referred to below as a RGB LED cluster. These LEDs may be operated in any one of a number of combinations to provide a specific color of light, color shows or patterns that are aesthetically pleasing to a user. For example, the LEDs may be operated as described in commonly assigned International Publication No. WO2005/003625, US Publication Nos. US 2005/0169812 and US 2005/0169666, all of which ate incorporated herein by reference.

Those skilled in the art will realize that various constructions for a base structure for supporting the LEDs, the white light source 18, and the various circuitry and electronics for supporting the functions of the device 10 can be provided. In the embodiment shown in FIG. 1, a base is the supporting function is provided by the male connector 13 and the board 14. Thus, the term base, as used herein, refers to any structure that supports the various components of the disclosed devices.

The outer shell 11 may act as a light diffuser, to cause a user to perceive the intended color, rather than the activation of distinct LEDs of different colors. Alternatively, a separate diffuser may be provided inside the outer shell 11. The shell 11 operates to combine the lights from the different LEDs to form a single color, the perception of which is dictated by the relative intensities of the individual colored LEDs. In other embodiments, no diffuser at all may be used, in order to allow a user to simultaneously perceive multiple colors of the different LEDs.

Also, when indoor insect control is an issue, the lighting effects may be programmed to attract or repel insects, using conventionally known lighting techniques for the same. The diffuser 11 may also act is a fragrance dispenser as the walls of the diffuser 11 may absorb fragrance or other active ingredients or the diffuser 11 may include inner and outer walls with a void space therebetween that accommodates a fragrance oil or other volatile active.

Figure 2:
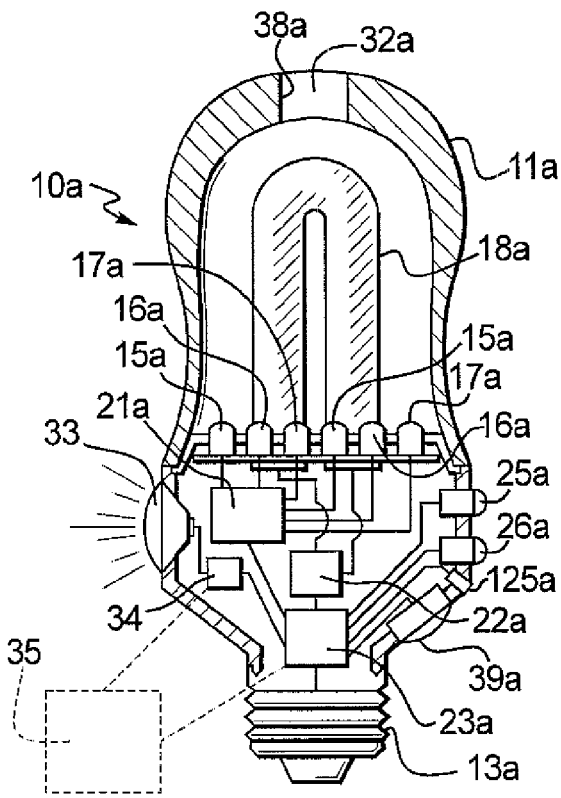
FIG. 2 is a cross-sectional view of another disclosed outdoor device with a threaded, screw-in base and a fluorescent white light source.

The incandescent bulb 18 can provide a primary source of illumination for the device 10 but the more preferable method is to employ a fluorescent lamp like those shown and FIGS. 2 and 5 as a white light source. Alternatively (or in addition), the red, green, and blue LEDs 15-17 may be configured to, in combination, produce white light, when their respective wavelengths are mixed by a diffuser or the like. Examples of a RGB LED cluster producing white light can be found in commonly assigned Provisional Application No. 60/641,441, which is incorporated her herein by reference. See also the "white light area" of the CIE chart of FIG. 4 below. Other white light sources, such as halogen or other types of fluorescent lights as well as white LEDs may also be used as a primary white light source.

Figures 13, 14:
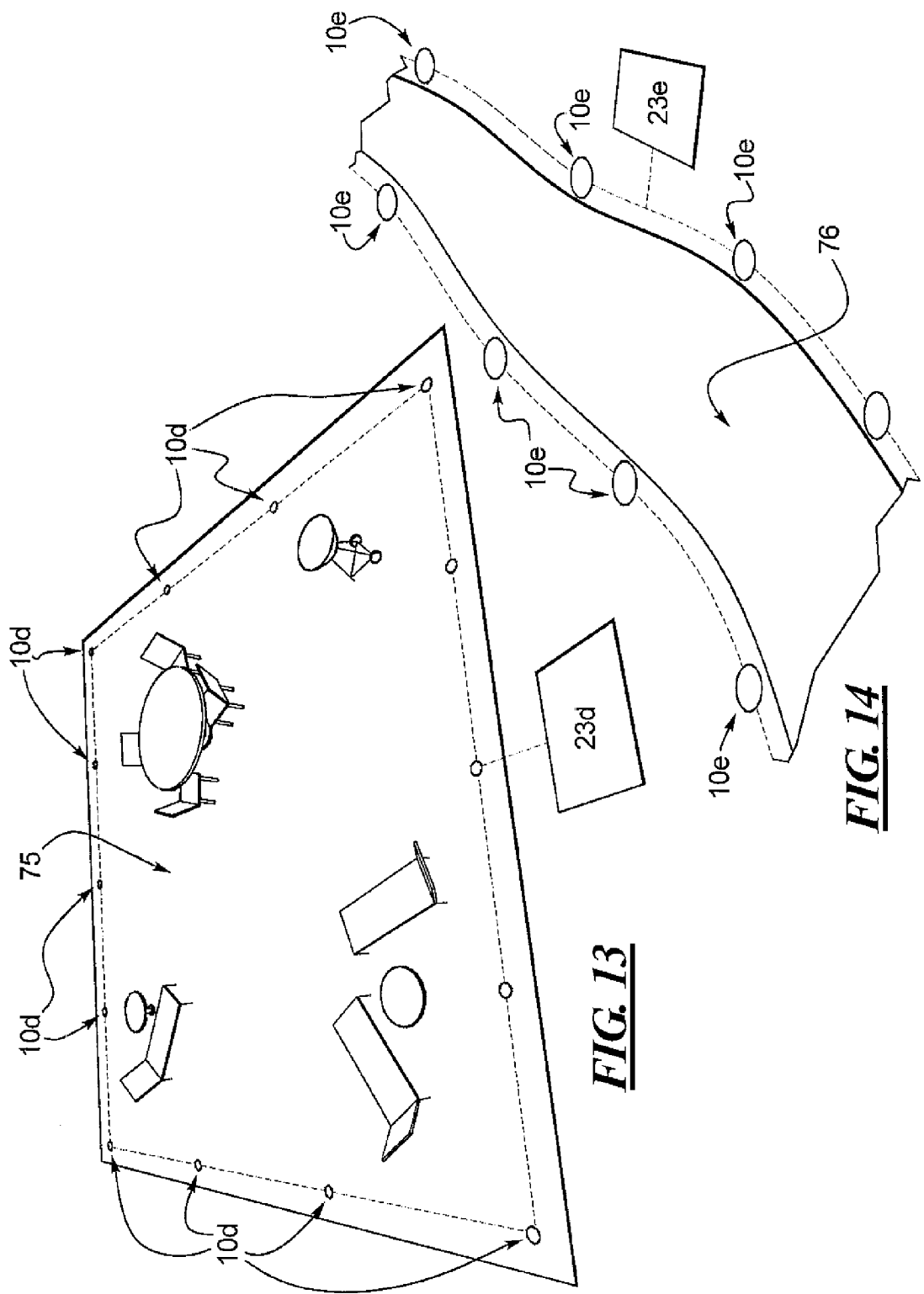
FIG. 13 is a plain view of an outdoor lighting system made in accordance with this disclosure as installed around a patio.
FIG. 14 is an outdoor lighting system made in accordance with this disclosure as installed along a walkway or path.

Power is supplied to the LEDs by the circuit 21 and power supply to the incandescent bulb 18 by the circuit 22. These circuits, in turn, are controlled by the microcontroller circuit 23 which is also linked to the volatile active heater 24, the ambient light or motion sensor 25 and the ambient sound sensor 26. In single, stand-alone devices, the microcontroller circuit 23 includes a memory for storing one or more light shows carried out by the LEDs 15-17 as coordinated with the white light source 18 and the release of the active from the volatile active cartridge 27. The memory of the control circuit 23 may be supplemented or changed using replacement chips or boards such as the one shown at 28 and FIG. 3 which is inserted into the remote control 29. The memory of the controller circuit 23 may also be supplemented by the volatile active cartridge 27 which may be equipped with its own memory or memory card, the contents of which are then communicated to the control circuit 23. In integrated outdoor systems, the controller 23 would serve as a network interface with a primary controller 23d or 23e as shown in FIGS. 13-14.

An additional volatile active dispenser is of shown at 32 in FIG. 1 which, in this embodiment, does not include its own heater such as that shown at 24 for the cartridge 27, but which relies upon heat generated by the incandescent bulb 18. Of course, the dispenser 32 could also be controlled using heat dispensed by a heater and controlled by the controller 23.

Turning to FIG. 2, the device 10a includes an inverted u-shaped fluorescent lamp 18a instead of an incandescent white light source. The shell 11a includes a single volatile active cartridge 32a as well as a speaker 33. The speaker 33 is coupled to an audio circuit 34 which, in turn, is coupled to the control circuit 23a. The control circuit 23a is wirelessly coupled to an exterior audio system 35. The audio system 35 may also be wirelessly coupled to the audio circuit or sound card 34. Similar to the device 10 shown in FIG. 1, the device 10a also includes a light or motion detector 25a, a sound detector 26a, and one or more RGB LED clusters 15a, 16a, 17a. The clusters are controlled by the circuit 21a and the fluorescent tube 18a is controlled by the circuit 22a.

Thus, the devices 10, 10a of FIGS. 1 and 2 can both be responsive to ambient conditions such as the light through the light or motion sensors 25, 25a and sound through the sensors or microphones 26, 26a. Temperature sensors 125, 125a may also be employed. The device 10a can generate sound and also be a part of a larger auxiliary sound system 35 as shown in FIG. 2. Used either indoors or outdoors, the device 10a can effectively provide background music and sound can be a part of a light show carried out through the RGB LED clusters by the circuit 23a and/or a central controller 23d, 23e as shown in FIGS. 13-14.

Figure 3:
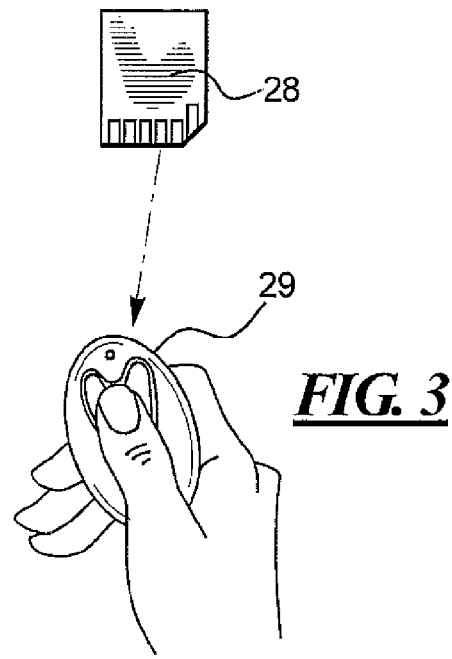
FIG. 3 illustrates a remote control with a combination light show/temperature control memory chip for used with the outdoor devices disclosed herein.

Obviously the stand-alone devices disclosed herein are complex and therefore a user interface of some sort is required. Buttons 39, 39a can be placed on the devices 10, 10a themselves or, the devices 10, 10a can be manipulated using a remote control 29 as shown in FIG. 3. A remote control 29 can also be used for manipulating or supplementing the memory of the primary circuit boards 23, 23a. Thus, an auxiliary/replacement/refill chip 28 can be provided and conveniently inserted into the remote 29 as shown in FIG. 3. The chip 28 can also be used to control the amount of heat delivered to the active cartridge 27 in addition to changing in the light shows. Further, the memory of the circuit boards 23, 23a and/or memory chip 28 can be used to increase or decrease the amount of active released as a light show progresses. Specifically, it maybe desirable to increase or decrease the amount active released during certain parts of the show. It may also be desirable to stop the release of actives during a show.

Although a single button or switch 39, 39a are shown in FIGS. 1-2 for exemplary purposes, any one of a number of user interfaces may be used so that the user may adjust the setting of the devices 10, 10a such as interfaces including one, two, three or more buttons. A removable lanyard-type switch may also be employed. Possible adjustments made include changing the color of the light emitted from the LEDs 15-17, adjusting the brightness of the LEDs 15-17, switching between white light, colored light, and off settings, scrolling through the various light shows available in the memory of the device, adjusting the evaporation rate of the fragrance or active (e.g., by adjusting the heat level, when a heat assisted device is used), volume adjustment, muting, freezing a show or setting, and/or setting predetermined programs for light shows or active emission changes that may be stored in a memory and operated by a processor (as discussed in more detail below). In preferred embodiments, the user interface is a button or switch that may be toggled to change the operation of the device 10 between different predetermined settings. For example, some suitable user interfaces are described in commonly assigned U.S. application Ser. Nos. 10/561,822 and 11/327,167, which are also incorporated herein by reference.

The heater 24 is preferably a resistance heater but other heating elements, such as positive temperature coefficient (PTC) heaters may be employed. Heat is applied to increase the evaporation rate of fragrance oil, fragrance gel, insecticide, insect repellents insect attractant, air sanitizer, deodorizer, medicine, aromatherapy material or the like. In other embodiments, fan-assisted evaporation devices, piezo-electrically actuated atomization devices, and/or unassisted fragrance dispensers may be substituted. Unassisted volatile active dispensers may simply include venting mechanisms that expose the volatile active to the ambient environment, or other such designs that enhance/provide convective airflow across a volatile active delivery medium. Of course, if unassisted volatile active dispensers are used, power need not be provided to the dispenser. These alternative devices ate known in the art, and will not be described in detail herein.

It will be noted here that if a white light source is utilized, heat from the white light source may be sufficient for satisfactory emission rates for many volatile actives. When the colored LEDs are being operated without white light, supplemental heating may be used. Mechanical fans may be used to enhance distribution or may be used instead of heating elements.

Regarding the use of insect control actives, the disclosed devices may be particularly useful for patio/deck lighting and outdoor promoter lighting where it is desirable to keep insects away from a defined area such as a patio, deck or pool area and/or word is desirable to attract insects away from such a defined area. Still further, use of the disclosed devices in an enclosed area such as the closet provides the opportunity for the volatile active to be a moth, cockroach, housefly, fruit fly, ant, gnat or other household insect killer or repellent.

Therefore, ingredients suitable for inclusion in the evaporative cartridges disclosed herein, or passive dispensers disclosed herein, is a fragrance, air freshener, deodorizer, odor eliminator, malodor counteractant, insecticide, insect repellant, mood enhancer, or the like, in liquid, oil or gel form, although gels and oils are preferred.

Preferably, if a fragrance is to be dispensed, the fragrance or ail freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals ate known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone of in combination with natural oils are described in U.S. Pat. Nos. 4,324,915, 4,411,829; and 4,434,306, which are incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use with the devices disclosed herein.

Suitable insect repellents, insect attractants and insecticides are well-known and will be apparent to those skilled in the art.

Returning to FIGS. 1 and 2 preferably, a compartment or recess 37, 38 (1) of 38a (2) is provided to receive the volatile active cartridges 27, 32, 32a which are replaceable. Any one of a number of known mounting mechanisms may be used to removably secure the cartridges 27, 32, 32a in the compartment 37, 38, 38a, but preferably, the cartridge slides into its respective compartment so as to become wedged therein, or snaps into place using a system of mating protrusions and recesses. This allows the user to easily remove and replace spent cartridges, such as reservoirs containing fragrance oils, with the oils being communicated from the reservoir to the ambient environment with or without a porous wick, or gel cartridges which, when mounted, expose a gel impregnated with fragrance to the ambient environment. Bottle-type cartridges are also possible.

Turning to FIG. 4, the intensity and exact color of the light emitted from the housings 11, 11a of the devices 10, 10a may be varied by changing the current applied to each diode 15-17, 15a-17a. The different combinations of LED operations will alter the perceived color when the light from the LEDs is diffused to form one perceived color. This is best understood in connection with the CIE chart with three coordinates 41, 42, 43 corresponding to three different-colored (RGB) LEDs respectively. The light show as described herein includes starting and ending color points and proceeding along any predefined path between those two points during the course of a show. This is explained in greater detail in pending Provisional Application No. 60/641,441, which is also incorporated herein by reference.

A color point refers to the settings of the LEDs at a given moment of the light show, which provides a specific perceived color. As the settings of the LEDs change over time in accordance with the instructions for the light show, the color points can ultimately be perceived as a "wash" or "waves" of colors. Because "perceived" colors are being discussed herein, the starting color point does not directly correspond to the wavelengths of light emitted by the LEDs used in the color show, inasmuch as those wavelengths are substantially constant. The starting and ending color points can, however, be defined by coordinates on the CIE chart.

The color points can also be defined by the relative intensities of the lights emitted from the LEDs used to produce the color show (i.e., the operational settings for the different LEDs at specified points of the light show). For instance, a color point can be defined by the specific intensity level set at that point in time for each LED being used, and the dominant wavelength of each LED. Preferably, intensity levels will be defined by the pulse widths of the LEDs (e.g., as a percentage of full intensity of the LEDs).

It will be understood by one of ordinary skill in the art that the combination of the lights from different-colored LEDs at specified intensities will directly correspond to a set point on the CIE chart. Therefore, the different possible methods discussed above for defining the color points (i.e., using CIE chart coordinates of specific LED settings) are substantially equivalent for purposes of defining a perceived color.

It will be noted, however, that there are many ways in which the lights from the different LEDs can be combined. In some methods, especially where diffusers are not used and the LEDs are merely placed in close proximity to each other, a user may perceive different colors close to the emission points of the LEDs. When color points are discussed, the reference is to the color of a substantially complete mixture of the lights from the different LEDs, even though there may be observable portions of the display in which the user sees distinct colors corresponding to the wavelengths from the individual LEDs, rather than the complete mixture.

The starting and ending color points are similar to the first and last entries in a look-up table setting forth all of the points of a color show in a conventional system; however, instead of providing all of the intervening points from the conventional look-up table, one can dispense with the need to determine and store each and every intervening color point. To achieve this effect, timing information is provided. The timing information defines timing aspects of the light show and LED control.

Using the timing information, the microcontrollers 23, 23a, 23b of FIGS. 1, 2 and 5 or 23d, 23e of FIGS. 13-14 may calculate all of the intervening color points for the light show on its own. This saves valuable memory space that would otherwise have to be devoted to complex look-up tables for various light shows. The timing information preferably includes information concerning the duration of the show, from display of the starting color point to the ending color point. The timing information also preferably includes information concerning the ramp speed for the LEDs, either as a whole, or individually. The ramp speed refers to the speed of intensity change of the LEDs. Generally, ramp speed may be defined as the unit of time it takes the LED to change one intensity level (for that particular show), with each intensity level being equal. Ramp speed can also be defined as the change of intensity per unit of time.

In contrast to using a color chart as shown in FIG. 4 or a set of look-up tables, an algorithm can be developed for controlling the color temperature of a light or light object. The term "color temperature" generally is used herein in connection with white light, although this usage is not intended to limit the scope of this term. Color temperature essentially refers to a particular color content or shade (e g., reddish, bluish) of white light. The color temperature of a given radiation sample conventionally is characterized according to the temperature in degrees Kelvin (K) of a black body radiator that radiates essentially the same spectrum as the radiation sample in question. The color temperature of white light generally falls within a range of from approximately 700° K (generally considered the first visible to the human eye) to over 10,000° K.

Ironically, lower color temperatures generally indicate white light having a more significant red component or a "warmer feel," while higher color temperatures generally indicate white light having a more significant blue component of a "cooler feel". For example: fire has a color temperature of approximately 1,800° K; an incandescent bulb has a color temperature of approximately 2848° K; morning daylight has a color temperature of approximately 3,000° K; and an overcast sky has a color temperature of approximately 10,000° K. A color image viewed under white light having a color temperature of approximately 3,000° K has a relatively reddish tone, whereas the same color image viewed under white light having a of approximately 10,000° K has a relatively bluish tone.

Thus, color temperature algorithms can be used to change the "mood" provided by a light or light object. Color temperature algorithms could also be provided for various times of the day and the seasons of the year. Color temperature algorithms can also be used for festive occasions, pet training or in response to sounds made by pets or children for purposes of soothing or calming.

The LEDs may be controlled by pulse width modulation (PWM) such that the pulse width of a constant current applied for a portion of the duty cycle is varied to alter the intensity of the light emitted from the LED. The intensity level of the LED can be measured as a fraction of the duty cycle during which the constant current is applied, which, among other ways, can be expressed as a percentage. When an LED is not on, the pulse width is at 0%. When a constant current is applied to the LED for half of the duty cycle, the intensity of the LED is at 50%. Ramp speed maybe defined as the amount of time between changes of intensity of one percentage point of total intensity. Consequently, if the ramp speed of an LED is set at two seconds, then during the course of the light show that LED will change its intensity by one percentage point every two seconds until reaching the target value (i.e., the intensity value of the LED for achieving the ending color point). In an embodiment, ramp speed is defined as the percentage change per second. Of course, the speed can be defined in any one of a number of ways, as would be understood by one of ordinary skill in the art. Also, the ramp speed can be a positive or negative value, depending on whether the intensity of the LED is to be increased or decreased during the light show. Alternatively, the microcontroller 23 can be programmed to increase or decrease the intensity setting by comparing the starting intensity setting to the ending intensity setting. Thus, for instance, if the microcontroller 23 determines that the value of the ending setting is lower than the value of the starting setting, the microcontroller 23 will decrease the intensity of the LED at a rate set by the given ramp speed.

With the timing information provided, the microcontroller 23 controlling the LEDs 15-17 can be provided with logic that calculates the intervening color points between the starting and ending points of the CIE chart of FIG. 4. The logic reads the timing information from memory and adjusts the duty cycle for each LED in accordance with the ramp speed and target intensity. The intensity for each LED is adjusted until the target value is reached or the duration of the show has been reached. At this time, the microcontroller 23 will read the next set of timing information from memory and begin again. Of course, if the target intensity is reached prior to the duration of the show, the microcontroller 23 will hold the intensity of the LED until the duration is reached. If a continuously changing show is desired, the ramp speed may be set such that the target intensity is not reached prior to the duration of the show and thus, the target value will never be reached. Likewise, the microcontroller may be configured to ignore the duration, and load the next intensity and ramp speed as soon as the target intensity is reached.

The programming for achieving this would be readily understood by one of ordinary skill in the art. Accordingly, a detailed description of the many different ways of programming the microcontroller will not be provided herein.

FIG. 5 shows the device 10b that includes a globe or shell 11b with a top opening 38b therein for accommodating a distal end 45 of a cylinder 46 filled with active 47. The cylinder 46 is disposed axially with in a coiled fluorescent lamp (CFL) 18b which is controlled by the circuits 22b and 23b. The circuit or controller 23b is also linked wirelessly to an exterior sound system 35b which includes its own speakers 33b. Of course, a speaker may be incorporated into the device 10b as well. Further, the device 10b can be equipped with an ambient light or motion detector, sound detector and additional active dispenser equipped with a heater.

As discussed above, the components for emitting light/active/sound may be configured to work in coordination with each other in any one of a number of ways. Provided herein axe preferred embodiments for configuring and controlling the various disclosed devices to emit light and fragrance. These are, however, only preferred embodiments, and numerous other configurations ate possible.

FIG. 6 shows a circuit diagram for one control arrangement for operating a device 10 that produces a coordinated/combined presentation of light and volatile active. A microcontroller (or ASIC) 23 controls the operation of the device 10. Power is supplied to the system 499 through a lamp (AC power source 660). A voltage conversion device 610 converts the AC voltage from the AC power source 660 to a DC voltage. A microprocessor 23 receives power from voltage conversion device 610 and controls the operation of system 499 using the received power.

Still referring to FIG. 6, the microcontrollers 23, 23a, 23b or 23c (FIG. 12) include a control logic 440 that provides the operational instructions to the various elements of the device 10 in accordance with input signals or internal programs. The control logic 440 converts received signals or runs internal software routines to set the operation of the array of LEDs of 15-17 and/or the volatile active control system (e g., volatile active dispenser 27), with a resistor R1 acting as the heater 24.

The control logic 440 sends a signal for controlling the operation of the array of LEDs to LED control block 410. When using pulse width modulation to drive and control the LED array, the LED control block 410 sets the duty cycles for the LEDs based on the instruction from the control logic 440.

The control logic 440 may also control auxiliary devices such as a sound card 34, which in turn, and may be linked to speakers 33 associated with the device 10 or speakers 33 associated with an auxiliary audio system 35. The auxiliary audio system 35 may be a CD player, a computer, or an interface to an MP3 player. The control logic 44 may also be linked to the light/motion, sound and temperature sensors 25, 26, 125 respectively. Other alternatives will be apparent to those skilled in the art.

Supply lines 412a-412c supply voltage across resistors 414a-414c, from power supply 404. Preferably, the voltage supplied across resistors 414a-414c is between about 3.5 and about 5 0 volts. Resistors 414a-414c in turn power a red LED 15, a green LED 16, and a blue LED 17, respectively. Field effect transistors (FETs) 418a-418c are turned on and off in accordance with the respective duty cycles generated by the LED control block 410. Operation of the FETs 418a-418c control the RGB LEDs 15-17 to be activated for the portions of the duty cycle set by the LED control block 410. Thus, the intensity and color of the light emitted from the LEDs 15-17 can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the intensity of the diode appears constant to an observer (with no discernable flicker), until the set period of activation over the duty cycle is changed.

While six colored LEDs 15-17 or two clusters are shown with respect to the device 10, 10a in FIGS. 1-2, any number of LEDs or RGB LED clusters may be used. In addition, the choice of which color LEDs to provide may be dictated by design preferences.

Generally, one of each color LED will be provided in close proximity to one of each other color. With such a cluster arrangement, the exact color of each diode of the set of three different colors can be adjusted to create a blended color, for example, amber of purple. This blending can be achieved by providing the three diodes in such close proximity that the observer only sees the blend of colored lights, rather than each individual diode. Alternatively, or in addition, a diffuser may be provided to diffuse the light of the three diodes to produce the combined color. In other embodiments, the lights may be projected off of a surface to be combined before being viewed by an observer. When the LEDs ate not placed close to each other; or there is not sufficient diffusion, multiple colors may be perceived in the device 10. This is a matter of design preference.

LEDs of a wide array of colors ate readily available from lighting manufactures. Also, the arrangement and operation of LEDs to achieve a desired presentation would be apparent to one of ordinary skill.

In addition to monitoring ambient temperature using the sensor 125, the microprocessor 23 may monitor the temperature delivered to the active cartridge 27 through the use of a temperature sensor 61. In this case, as shown in FIG. 6 the microprocessor 23 can adjust the current through the heating resistor R1 to keep a constant temperature to the active cartridge 27 regardless of the orientation of the bulb or fixture used. Thus, the proper amount of heat is provided to the cartridge 27 regardless of the type of white light source (incandescent, fluorescent, coiled fluorescent or white LED) or the orientation of the white light source. The sensor 61 provides feedback to the microprocessor 23 so the correct temperature of the cartridge 27 is maintained. A switch SCR1 varies the current passing across the resistor R1, thus varying the heat produced by resistor R1 and the rate of vaporization of the volatile active. In alternative embodiments, the resistor R1 may be replaced and/or supplemented by a fan which is controlled by switch SCR1, or an atomization device. Also, switch SCR1 may be replaced by an FET in other embodiments. Further, the volatile active dispenser may also be mechanically adjusted by a user, rather than through a microprocessor. Different fragrances and different actives will require different temperatures for proper emission rates.

Additionally, the temperature sensor 61 and microprocessor 23 may adjust the heat to deliver more fragrance or active at one point in a particular light show and less fragrance or active at a different point or time in a particular light show to enhance the user experience. For example, certain color schemes of the light show may require more or less fragrance or active than other color schemes of a light show. By way of one example that is not intended to be limiting, it may be beneficial to emit more fragrance during a blue/green portion of the light show and less fragrance during a red/orange portion of the same light show. Other active emission rates can be controlled according to a light show or according to other outside sources such as exterior light or sound as recorded by a microphone 26, 26a, 26c, a light/motion detector 25, 25a, 25b as indicated in FIGS. 1-2 and 12.

The white light source 18, 18a may be connected to control block 410 (FIG. 7), or may be controlled through separate means, inasmuch as the white LED(s) (or other conventional white light source) is typically either on or off and is not necessarily subject to the same range of control (unless dimmers or the like are used). Such modifications, however, would be readily understood by one of ordinary skill in the art.

Still referring to FIG. 7, microprocessor 23, 23a may also control a use-up cue 420. The use-up cue 420 tracks the use of volatile active control to estimate the time at which the volatile active in the volatile active dispenser is likely to be used up. When the use-up cue 420 determines that volatile active has been spent, it sends a signal to LED control block 410 to cause the LEDs to illuminate in a pattern, color, or other manner to indicate to a user that it is time to replace the volatile active in the dispenser if a refillable dispenser is used, or more preferably, the volatile active cartridge shown at 27 in FIG. 1.

Returning to FIG. 6, the control logic 440 may be programmed/controlled in any number of ways. In one embodiment, an RF transceiver 448 receives an external signal, through an antenna 449, from a remote control. That signal is transmitted from the RF transceiver 448 to control logic 440 to set the presentation of light through the LED control block 410 and the volatile active control 650. Also, the operation of the control logic may be set by an internal program.

A user may manually set the volatile active output and light show. In this case, a program select switch 39, 39a, 39b (FIGS. 1-2 and 5) may be operated by a user to set a light show program for the LEDs 15-17. Of course, additional buttons or switches may be provided, depending on the level of the control and programmability desired. In particular, a switch can be provided to control whether manual or automatic operation/programming is desired.

Figure 8:
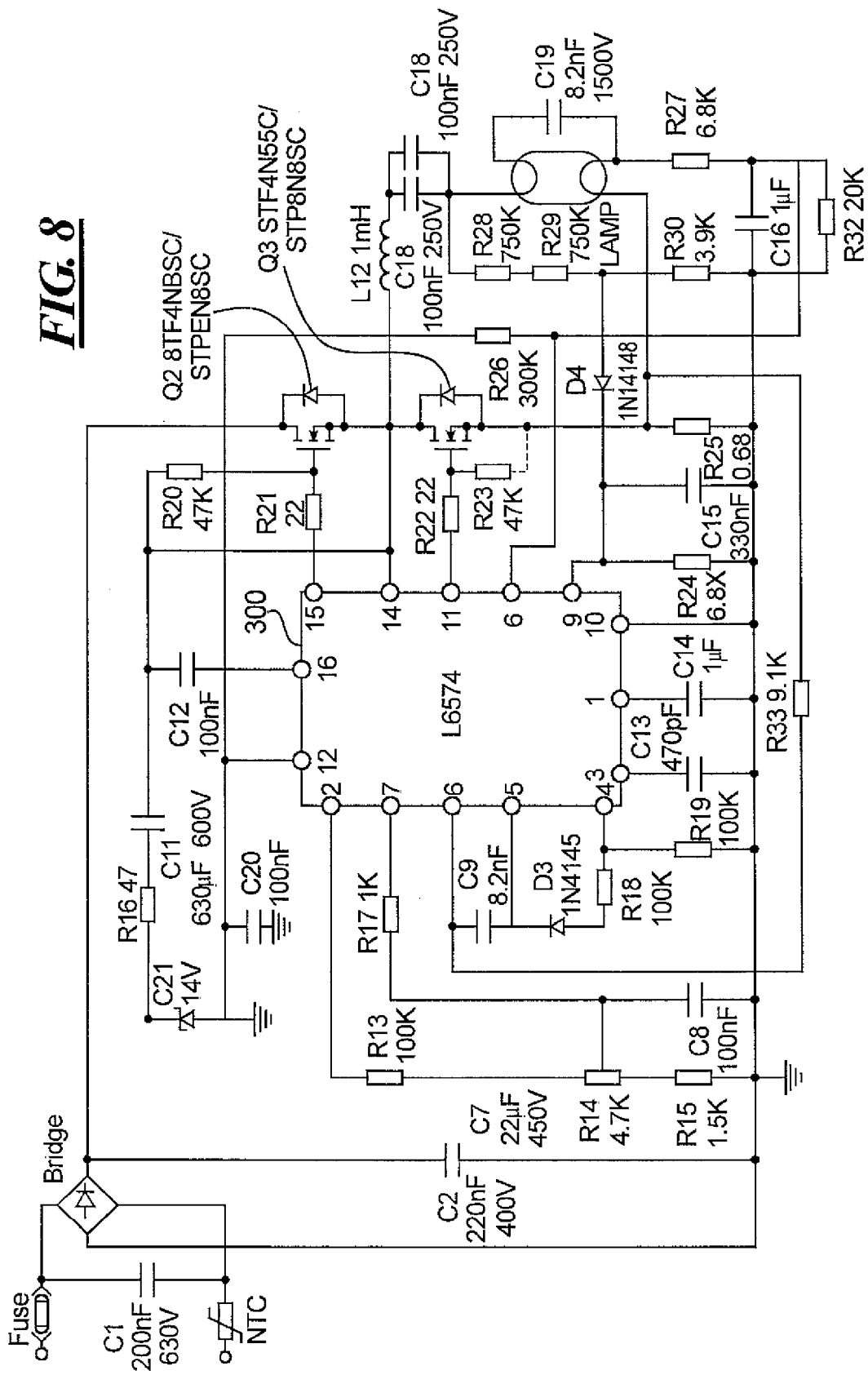
FIG. 8 is a circuit diagram of the ballasts for the coiled fluorescent lamp (CFL) white light sources of the devices shown in FIG. 5.

FIG. 7 shows one program for operating the control system shown in FIG. 8. One of ordinary skill in the art will appreciate that a wide variety of other programs may also be implemented to produce the desired control over the presentation of coordinated light and active. The program starts operation of the device at step S1. At step S2, it is determined whether operation of the microcontroller 23 is to be set manually by a user or automatically with a particular program. If manual operation is selected, the program proceeds to step S3. In step S3, the setting of the switch 39 is checked to set the level for operating the heater 24. For instance, in a first switch setting, the heater 24 is operated at a first temperature, while other temperatures may be set by other settings. In step S4, the operation of the switch 39 is checked. The system is set such that different preprogrammed light shows ate selected depending on how many times a user toggles the switch 39. Step S5 sets the light show from among an off setting, a variant light show, a strobe setting, emission of red light, emission of purple light, emission of blue light, emission of amber light, and emission of white light, depending on the toggling of switch 39.

If the automatic mode is set in step S2, the program proceeds to step S6, in which a default setting is provided for operation. This automatic setting may be set by information from a program set in the memory, a sensor reading, a remote control, the power supply (e.g., by toggling a light switch controlling the lamp in which the device 10 is positioned), or the like.

Returning to FIG. 6, microcontroller 23 may be an Amtel Mega8 processor. The memory 402 preferably is Microchip 24LC00 (manufactured by Microchip Technologies, of Chandler, Ariz.) or an Amtel AT25F512 (manufactured by Amtel Corp., of San Jose, Calif.). In other embodiments the memory 402 may be a memory chip or card 28 associated with a remote control 29, so that the light shows stored therein may be removed and replaced with other memory cards/chips 28. In this manner, the user can purchase new light shows and/or coordinate the light shows with the particular active ingredient that is being emitted.

Preferably, the memory 402 will store data concerning the light show, as discussed above. This data may include starting color points, ending color points, duration information for segments/shows, ramps speeds, other timing information, and the like. The microcontroller 23, 23a, 23b, 23d, 23e may have onboard program memory or external program memory containing the instructions for interpreting the light show data, calculating intervening light points, and controlling the LEDs based at least in part on the color data and timing information. Thus structured, memory 402 storing the light shows does not need the full range of data typically provided in look-up tables used to define light shows.

Figure 9:
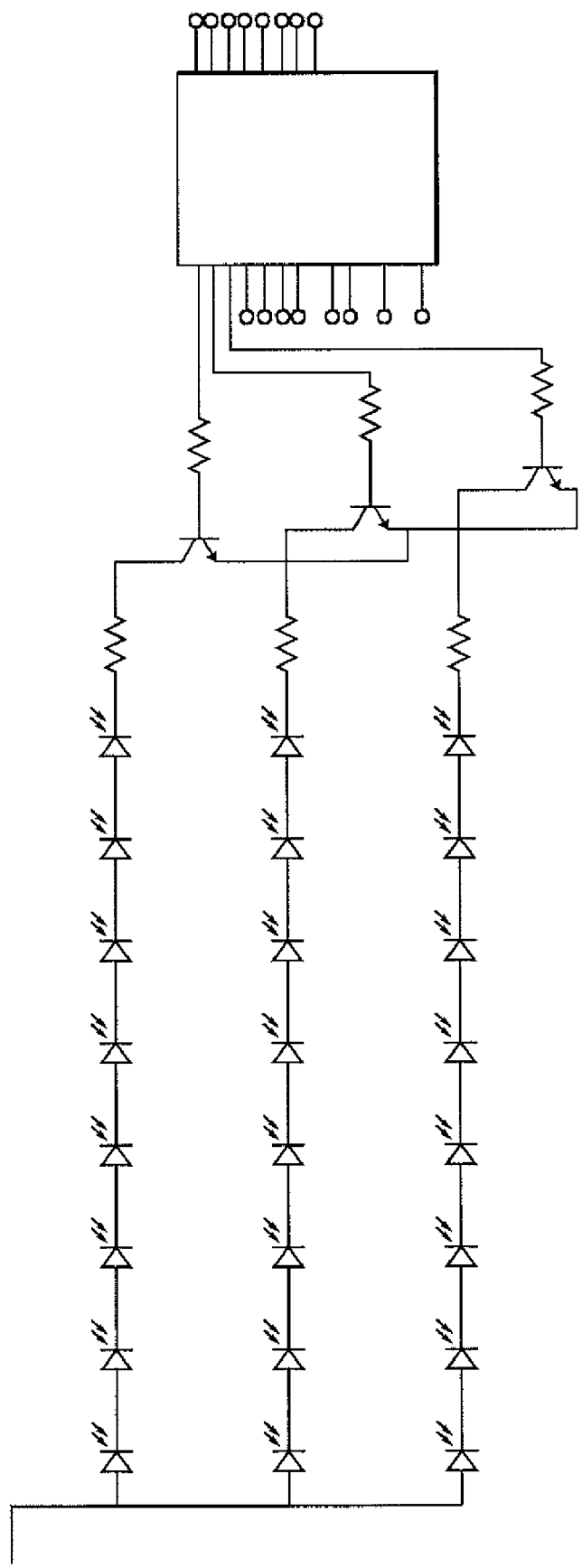
FIG. 9 is a circuit diagram for the LED drivers for the devices shown in FIGS. 1-2 and 5.
Figure 10:
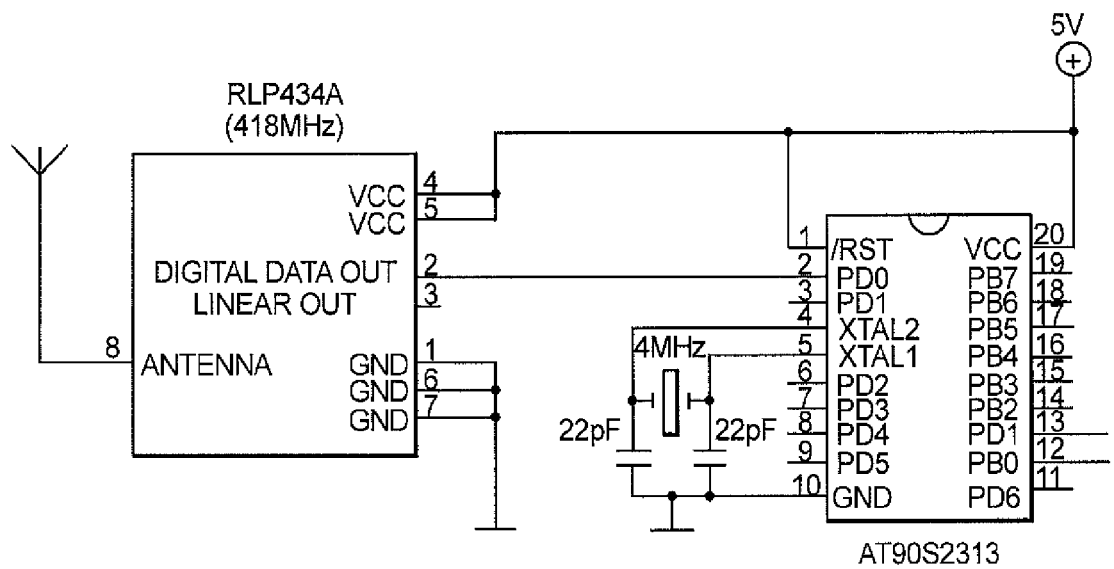
FIG. 10 is a circuit diagram for the radiofrequency (RF) receiver for the devices shown herein employing a remote control.
Figure 11:
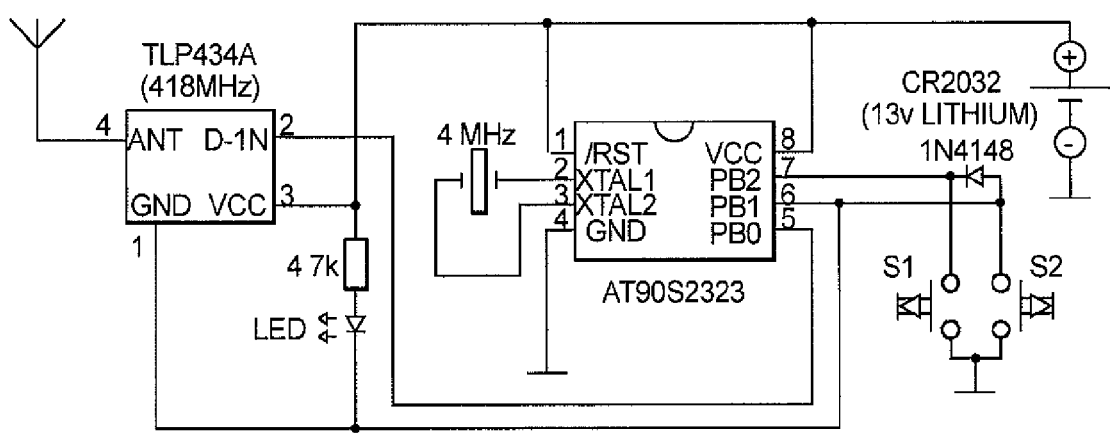
FIG. 11 is a circuit diagram of for the RF transmitter for the devices shown herein employing a remote control.

The size of the external memory 402a, 402b and extent of the program stored therein to instruct the controller 23, 23a-23e and the extent of the program stored onboard the microcontroller 23, 23a-23e in the manufacturing process can be determined based on design needs. Also, in future replacement memory cards 402, where such ate used, additional logic can be provided to control the microcontroller 23, 23a-23e, when additional information is needed to operate the new light shows. One of ordinary skill in the art would appreciate the different ways of dividing up such information between the memory 402 and microcontroller 23, 23a-23e. However, in a preferred embodiment, the system is defined such that microcontroller 23, 23a-23e contains the operating instructions for the light shows and the memory 402 contains the operating instructions for the light shows and the memory 402 contains the timing, intensity and ramp speed data for each LED used in the light shows A circuit diagram for a ballast for a fluorescent light 18a, 18b (see FIGS. 2 and 5) is shown in FIG. 8. Information regarding the ballast preheat and dimming chip 300 can be found at http://www.st.com/stonline/products/literature/ds/5654.pdf. Of course, other ballast designs will work and will be apparent to those skilled in the art. A LED driver circuit is shown in FIG. 9. The driver circuit shown in FIG. 9 is controlled by the microcontroller 23, 23a-23e. For those embodiments employing a remote control 29 (see FIG. 3), a suitable RF receiver circuit diagram is shown in FIG. 10 and a suitable RF transmitter circuit diagram is shown in FIG. 11, which is also driven by the microcontrollers 23, 23a-23e.

FIG. 12 illustrates a device 10e with a modified shell 11e that is detachably connected to the base structure 13e to convert the bulb-like device 10a shown in FIG. 1 to the floodlight configuration shown FIG. 12. All remaining elements of FIG. 12 are the same as those presented in FIGS. 1-2 and 5. The controller 23d operates in a manner similar to the controllers 23, 23a, 23b discussed above.

FIG. 13 illustrates in outdoor lighting scheme incorporating the devices of the present disclosure utilizing the devices 10d for lighting and outdoor patio 75. The devices 10d are linked wirelessly to a controller 23d which controls the light intensity, color scheme, color intensity, light show and/or light and sound show. FIG. 14 illustrates a similar concept where the devices 10e are used as low voltage lighting for a pathway 76. The controller 23e operates in a manner similar to the controllers 23, 23a, 23b discussed above.

Thus, the embodiments of FIGS. 1-2, 5 and 12 described above serve as replacements for a conventional outdoor light bulb and therefore can be used with conventional outdoor lighting systems. The light shows or colored light themes may be coordinated with volatile active emission as well as light shows or colored light can be used to set the mood when the volatile active is an aromatherapy material fragrance.

Additional light shows may be supplied by way of memory cards or chips either separate from or in connection with the replacement fragrance or active cartridges. Thus, the consumer can conveniently and inexpensively match the fragrance or volatile active with a LED light show or light theme. The refill cartridges may be directly connected to the controller or device conducting the LED light show or communication between the memory chip or memory card and the controller can be accomplished through RFID technology as disclosed above at 448 in FIG. 6. Fragrance or active vapor deliver may be constant for, each mode or may be varied as heater boost settings may be incorporated into the switch mechanisms for the devices that include a heating element. The heating elements can be designed to mimic the heat generated by a fluorescent bulb (140° F.) to keep a constant delivery of fragrance when the device is used for conventional white light or when the device is used for displaying a light show.

Switch mechanisms can vary greatly from a single switch, a toggle switch, a lanyard-type switch, one, two and three button type interfaces, rotating switches built in to either the base or housing and remote controls. Preferably, the fluorescent lamp is turned off during a LED light show as a LED light show generates light about equivalent to an 8W night light. Thus, leaving the fluorescent lamp on during the LED light show would be counterproductive in terms of enjoying the light show.

In a preferred embodiment the fluorescent lamp or coiled fluorescent lamp (CFL) is equivalent to a 60W incandescent light bulb. The use-up cue function 420 of FIG. 6 may either be a timer device, such as a 30 day timer, or may include a sensor to determine whether a cartridge is actually depleted. In any event, a sound function may be incorporated into the use-up cue.

These figures show only possible arrangements for configuring and controlling the disclosed devices. Many different embodiments may be constructed without departing from the spirit and scope of our invention. It should be understood that disclosure is not limited to the specific embodiments described in this specification. To the contrary, this disclosure is intended to cover various modifications and equivalent arrangements included within the spirit and scope of this disclosure as defined by the claims. The scope of the claims is to be accorded the broadest interpretation so as to encompass all such modifications, equivalent structures and functions.

INDUSTRIAL APPLICABILITY

The devices of this disclosure makes it possible to achieve an overall desired effect by providing mood lighting, active ingredient emission, functional white lighting and sound emission from a single device.

While only certain embodiments have been set forth, alternatives and modifications will be apparent from the above description to those skilled in the art. These and other alternatives are considered equivalents and within the spirit and scope of this disclosure and the appended claims.

What is claimed:

1. An outdoor light system comprising:
a plurality of devices linked to a central controller disposed remotely from each of the plurality of devices,
each device comprising a white light source, at least one light group comprising red, green and blue lights, and a replaceable insert containing a volatile active material, and a transducer for transmitting sound, and
the central controller comprising a memory for storing at least one light and sound show, the controller being programmed to simultaneously operate the plurality of devices to carry out the at least one light and sound show through the plurality of devices,
each light show comprising starting and target points corresponding to starting and target intensity levels for each of the LEDs off each of said devices with a segment extending continuously between the starting and target points and timing information for a duration of the segment for each of said devices,
the central controller being programmed to calculate a plurality of intermediate intensity levels for each of the LEDs for the duration of the segments for each of said devices based on the starting and target intensity levels and the timing information for each of the LEDs, and the central corns oiler controlling each of the LEDs to operate at each of the calculated intermediate intensity levels during the segments to present a continuous change in color during each segment, each starting and target points and each segment extending therebetween falling within an area of a CIE 1931 Color Diagram defined by the following sets of coordinates (0.70, 0.30), (0.19, 0.72), (0.14, 0.06).

2. The system of claim 1 wherein each device comprises a control circuit for receiving control signals horn the central controller.

3. The system of claim 2 further comprising a remote control wirelessly coupled to the central controller, the remote control comprising a slot for receiving a memory card programmed with at least one light and sound show, the memory card being wirelessly coupled to the central controller by the remote when the memory card is received in the slot.

4. The system of claim 1 wherein each device further comprises one or more sensors selected horn the group consisting of light sensor, sound sensor, motion detector and temper attire sensor and wherein the light and sound show selection is dependent upon one or more factors selected from the group consisting of the volatile active, ambient sound, ambient temperature, ambient movement and ambient light.

5. The system of claim 1 wherein the central controller performs one or more functions selected horn the group consisting of:
activating the light and sound show and mining off the white light sources; turning on the white light sources and deactivating the light and sound show; turning off both the white light sources and light and sound show; freezing the light and sound show; selecting a light and sound show horn a plurality of light and sound shows stored in the memory; adjusting the sound volume; muting the sound; and adjusting the rate of volatile active emission.

6. The system of claim 1 wherein each device further comprising a heater to heat the insert.

7. The system of claim 1 wherein each device is linked wirelessly to the central controller.

8. The system of claim 1 wherein each device comprises a motion detector that is linked to the central controller.

9. The system according to claim 1, wherein at least one active ingredient in the active ingredient insert is selected fern the group consisting of a fragrance, an air deodorizer, an insecticide, an insect repellant, an insect attractant, and combinations thereof.

10. The system according to claim 1, wherein each device comprises a light sensor or motion detector that is coupled to the light and sound show circuitry, wherein the light and sound show circuitry adjusts the light and sound show based upon ambient light intensity or motion detection.

11. The system of claim 1, wherein each device further comprises a microphone that is coupled to the light and sound show circuitry, wherein the light in sound show circuitry adjusts the light and sound show based upon ambient noise.

12. An outdoor lighting system comprising:
a plurality of combination colored/white light devices linked to a central controller disposed remotely from each of the plurality of devices, each device comprising to a white light source and at least one light group comprising red, green and blue lights, light control circuitry comprising a timer for displaying light of different color schemes over different but regular time periods, an outer shell enclosing the white light source, the light control circuitry and the red, green and blue lights, each device linked to a central controller, the central controller comprising a memory comprising a plurality of light shows, the controller simultaneously operating the plurality of devices to carry out a selected light show through the plurality of devices,
each light show comprising starting and target points corresponding to starting and target intensity levels for each of the LEDs of each of said devices with a segment extending continuously between the starting and target points and timing information for a duration of the segment for each of said devices,
the central controller being programmed to calculate a plurality of intermediate intensity levels for each of the LEDs for the duration of the segments for each of said devices based on the starting and target intensity levels and the timing information for each of the LEDs, and the central controller controlling each of the LEDs to operate at each of the calculated intermediate intensity levels during the segments to present a continuous change in color during each segment, each starting and target points and each segment extending therebetween falling within an area of a CIE 1931 Color Diagram defined by the following sets of coordinates (0.70, 0.30), (0.19, 0.72),(0.14, 0.06).

13. The system according to claim 12 further comprises a volatile active insert that is received in a compartment disposed in one of the outer shell or the base of each device.

14. The system according to claim 12 further comprising a remote control wirelessly coupled to the central controller, the remote control comprising a slot for receiving a memory card programmed with color scheme time intervals, the memory card being wirelessly coupled to the central controller by the remote when the memory card is received in the slot.

15. The system according to claim 12 wherein the central controller varies light emitted from the red, green and blue lights to adjust the total light emitted from the device from a cool red light to a warm blue light.

16. The system according to claim 12, wherein each device further comprises a light sensor or motion detector that is coupled to the central controller, wherein the central controller adjusts the color scheme based upon ambient light intensity or detected motion.

17. The system according to claim 12, wherein each device further comprises a microphone that is coupled to the light control circuitry, wherein the central control adjusts the color scheme based upon ambient noise.

18. An outdoor light device and outdoor light system comprising:
the light device comprising a white light source, a light show circuitry, and at least one light group comprising a red, green and blue light cluster,
the light and sound show circuitry of the light device being linked to a central controller comprising a memory for storing a plurality of light shows, the central controller disposed remotely front the light device,
the light device further comprising a replaceable insert containing a volatile active, the volatile active being matched with the plurality of light shows,
the light device further comprising an outer shell connected to the base and enclosing the white light source, red, green and blue cluster and light show circuitry,
at least one switch linked to the central controller for causing the central controller to perform the following functions
activating the light show and turning off the white light source,
turning on the white light source and deactivating the light show,
turning off both the white light source and the light show,
freezing the light and sound show,
scrolling through the plurality of light and sound shows stored in the memory off the central controller,
each light and sound show comprising starting and target points corresponding to starting and target intensity levels for each off the LEDs of each of said devices with a segment extending continuously between the starting and target points and timing information for a duration of the segment for each of said devices,
wherein the central controller is programmed to calculate a plurality of intermediate intensity levels for each of the LEDs for the duration off the segments for each of said devices based on the starting and target intensity levels and the timing information for each of the LEDs, and the central controller controlling each of the LEDs to operate at each of the calculated intermediate intensity levels during the segments to present a continuous change in color during each segment, each starting and target points and each segment extending therebetween falling within an area of a CIE 1931 Color Diagram defined by the following sets of coordinates (0.70, 0.30), (0.19, 0.72), (0.14, 0.06).

19. The device and system of claim 18 wherein the insert is received in a slot disposed in the light device, the light device further comprising a heater which engages the insert when received in the slot, the heater being controlled by the light show circuitry and the current supplied to the heater being dependent upon the active contained within the insert.

20. The device and system of claim 18 wherein the device further comprising a network interface and transceiver for communicating with the central controller and for communicating with and/or synching with like outdoor devices.

* * * * *

UNITED STATES PATENT AND TRADEMARK OFFICE
CERTIFICATE OF CORRECTION

PATENT NO. : 7,604,378 B2  Page 1 of 1
APPLICATION NO. : 11/548940
DATED : October 20, 2009
INVENTOR(S) : Jeffrey J. Wolf et al.

It is certified that error appears in the above-identified patent and that said Letters Patent is hereby corrected as shown below:

Column 16, Line 46: replace "corns oiler" with --controller--

Column 16, Line 55: replace "horn" with --from--

Column 16, Line 64: replace "horn" with --from--

Column 16, Line 66: replace "temper attire" with --temperature--

Column 17, Line 4: replace "horn" with --from--

Column 17, Line 6: replace "mining" with --turning--

Column 17, Line 11: replace "horn" with --from--

Column 17, Line 23: replace "fern" with --from--

Column 18, Line 51: replace "off" with --of--

Column 18, Line 54: replace "off" with --of--

Column 18, Line 60: replace "off" with --of--

Signed and Sealed this

Twenty-seventh Day of July, 2010

David J. Kappos
*Director of the United States Patent and Trademark Office*